Figure 1:
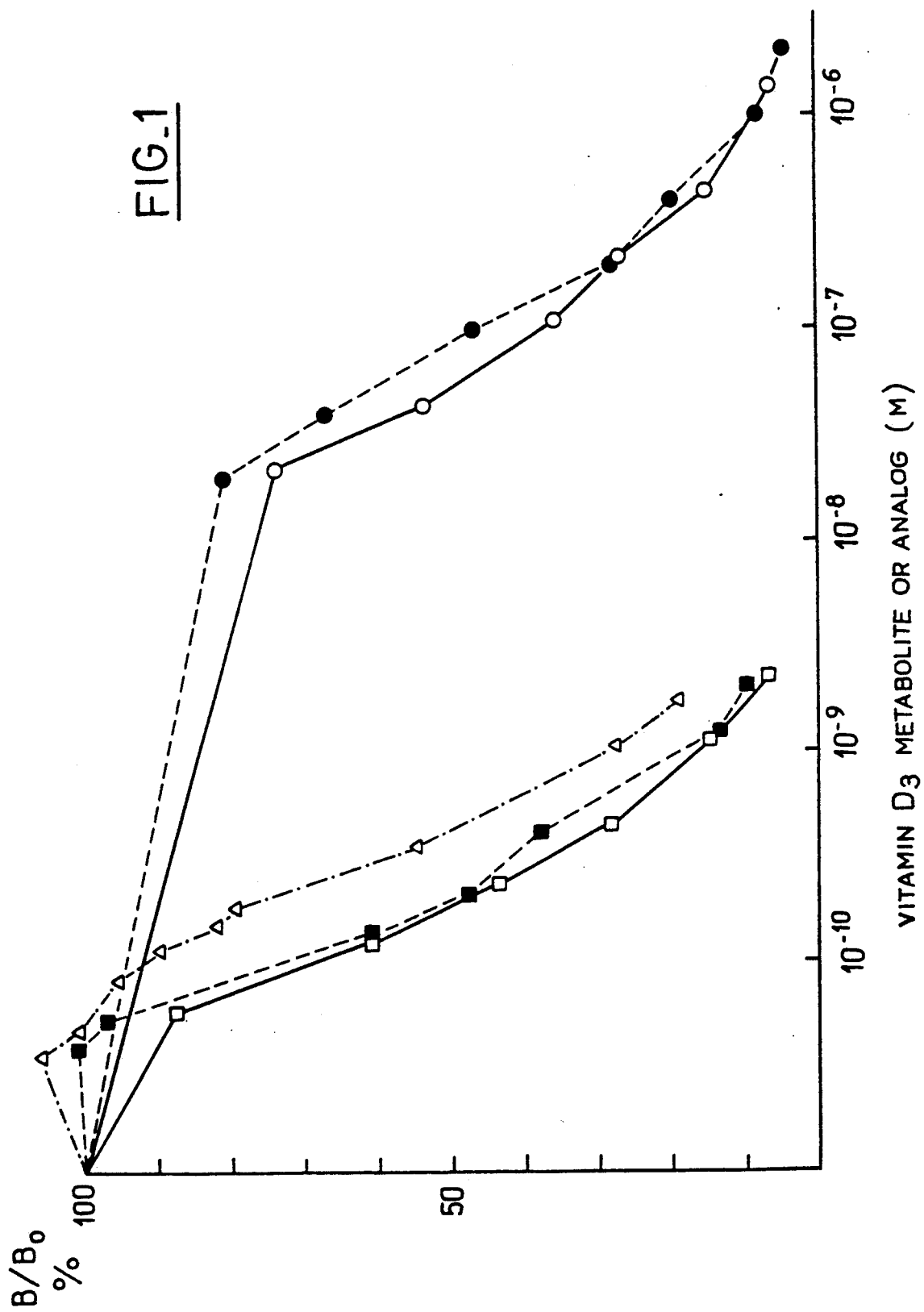

United States Patent

Bouillon et al.

[11] Patent Number: 5,093,519
[45] Date of Patent: Mar. 3, 1992

[54] VITAMIN D DERIVATIVES: THERAPEUTIC APPLICATIONS AND APPLICATIONS TO ASSAYS OF METABOLITIES OF VITAMIN D

[75] Inventors: Roger Bouillon, Herent; Pierre J. De Clercq, Gent; Pierre Eliard, Brussels; Maurits Vandewalle, Gent, all of Belgium

[73] Assignee: Ire-Medgenix S.A., Fleurus, Belgium

[21] Appl. No.: 345,623

[22] Filed: May 1, 1989

[30] Foreign Application Priority Data

May 4, 1988 [FR] France .................. 88 05985

[51] Int. Cl.$^5$ .................. C07C 35/21; C07C 69/34
[52] U.S. Cl. .................. 560/194; 558/155; 558/156; 558/194; 558/128; 556/449; 560/231; 562/498; 584/188; 584/310; 584/454; 584/456; 584/458; 568/33; 568/37; 568/62; 568/441
[58] Field of Search .................. 558/155, 156, 194, 428; 556/449; 560/194, 231; 562/498; 564/188, 310, 454, 456, 458; 568/33, 37, 62, 441, 591, 665, 704, 712, 713, 819

[56] References Cited

U.S. PATENT DOCUMENTS 4,898,855 2/1990 Baggiolini et al. .................. 514/167

FOREIGN PATENT DOCUMENTS

WO87/00834 2/1987 PCT Int'l Appl.
WO89/10351 11/1989 PCT Int'l Appl.

*Primary Examiner*—Richard L. Raymond
*Attorney, Agent, or Firm*—Cooley Godward Castro Huddleson & Tatum

[57] ABSTRACT

Vitamin D derivatives corresponding to the following formula I

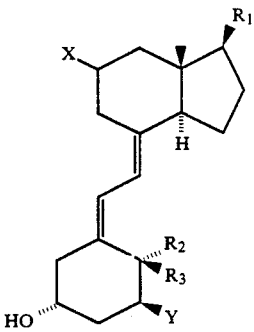

in which $R_1$ denotes a substituted alkyl group having 1 to 15 carbon atoms, in particular the side chains of vitamin $D_2$ ($C^{20}$ to $C^{28}$) or $D_3$ ($C^{20}$ to $C^{27}$), or these same chains partially modified, Y denotes H or OH or groups derived from the latter such as ester and ether;

X denotes an alkyl chain, in particlar of 1 to 6 carbon atoms, optionally substituted at different points by one or more functional group (s)

an unsaturated alkyl chain having one or more carbon-carbon double or triple bond(s), it being possible for these chains, in addition, to bear functional groups, or an aromatic or heteroaromatic ring, optionally substituted with halogens, one (or more) hydroxyl, amine, formyl carboxyl, thiol, cyano or nitro group(s), or alternatively groups derived from these latter, such as ether, ester, acetal or amide, or a halogen, a cyano, sulfoxide, sulfone, hydroxyl, thiol or amine group, or alternatively derivatives of these latter, such as ether, ester, amine and hydrazine;

(Abstract continued on next page.)

$R_2$ denotes a methyl group and $R_3$ an H, or $R_2$ is H and $R_3$ is methyl, or $R_2$ and $R_3$ are H, or alternatively $R_2$ and $R_3$ together denote a methylene group $=CH_2$.

The present invention relates to the therapeutic application of these derivatives.

The present invention also relates to a method for preparing these derivatives; and to an antigen prepared by the covalent binding of these derivatives with an immunogenic carrier protein and antibodies prepared using this antigen. Finally, the present invention also relates to tracers consisting of the conjugation of a derivative according to the invention with a labeling component such as an enzyme or an iodinated molecule, as well as to an assay method for metabolites of vitamin D comprising the use of these tracers as a reagent.

8 Claims, 4 Drawing Sheets

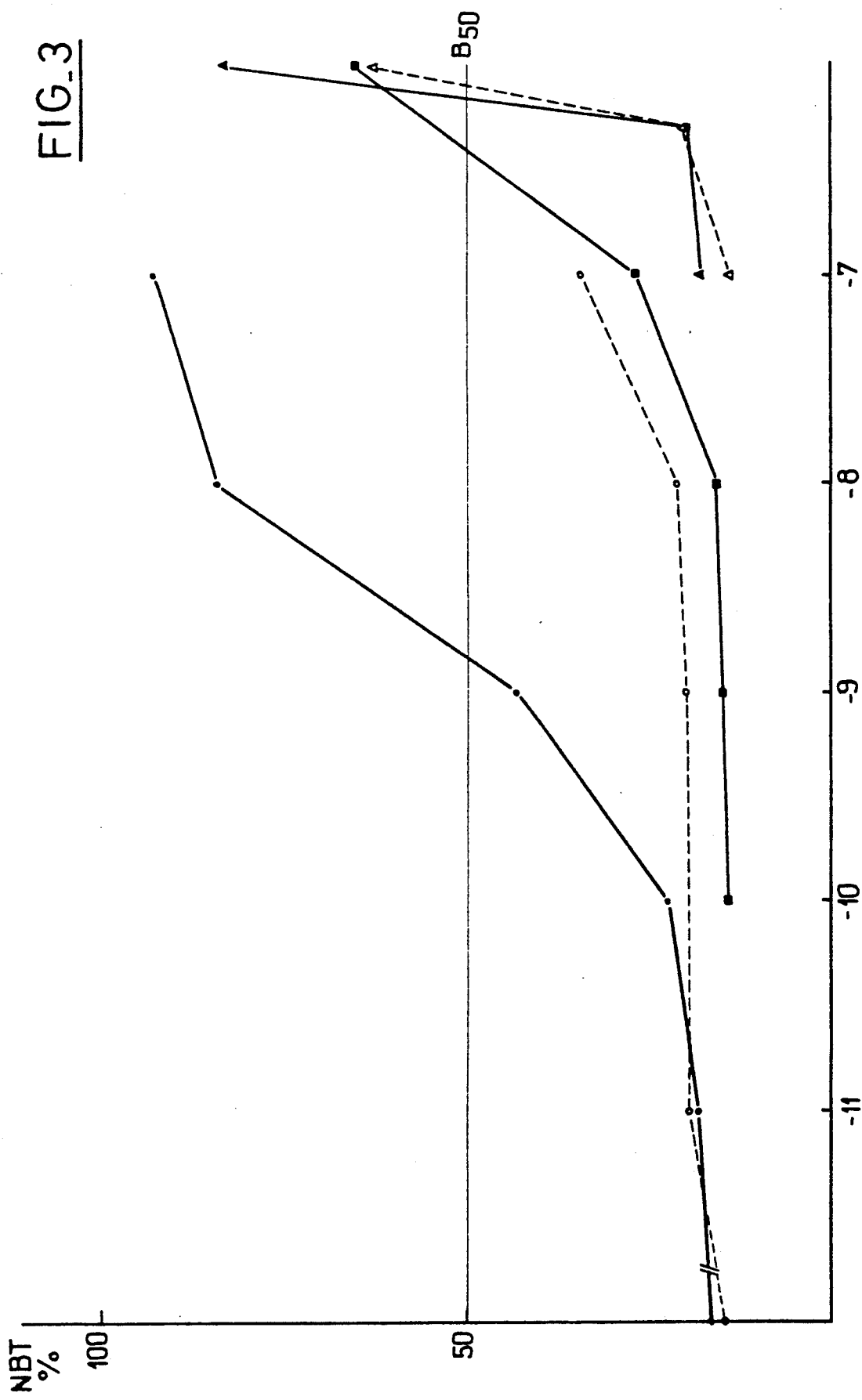

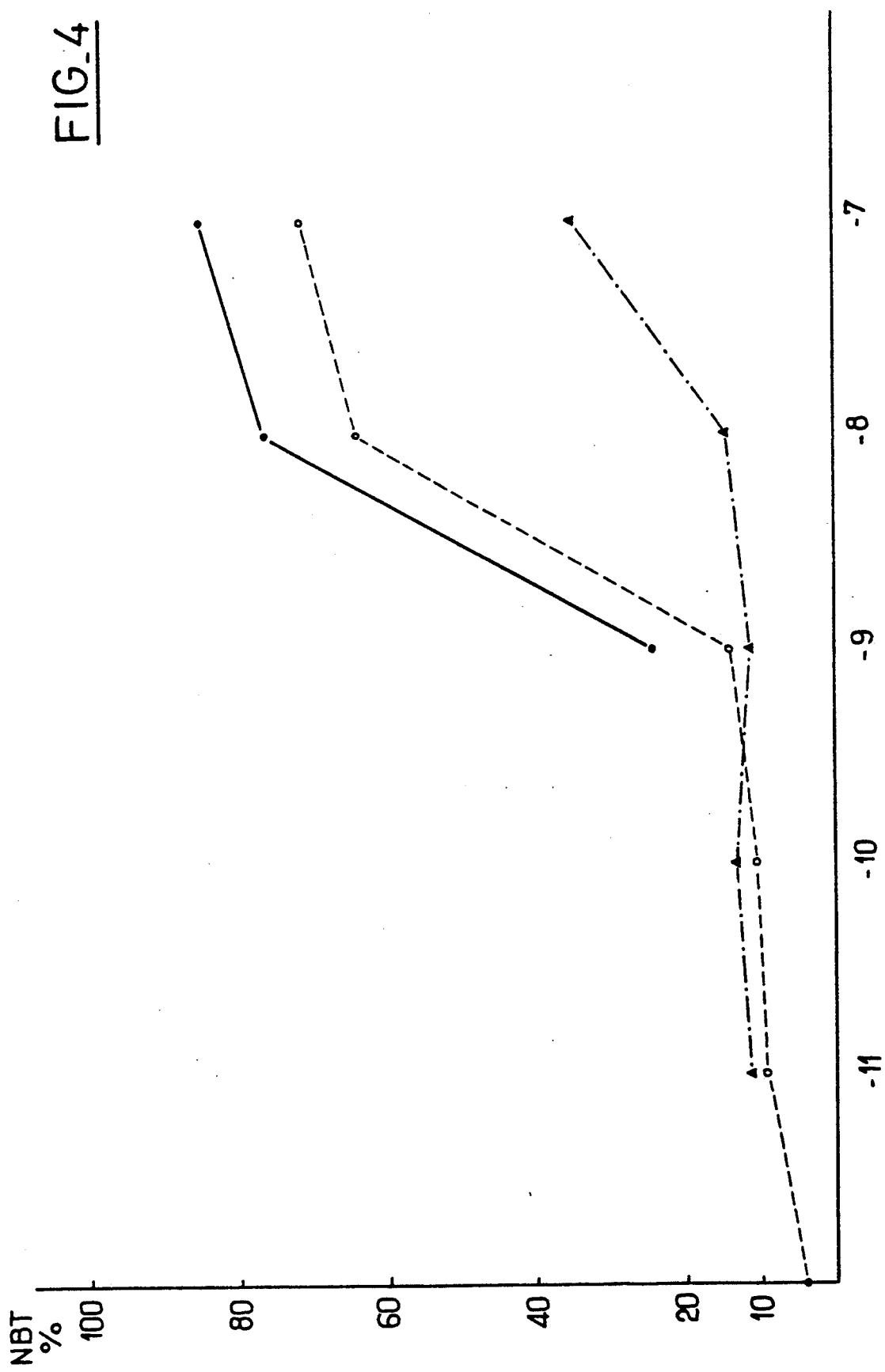
FIG_4

VITAMIN D DERIVATIVES: THERAPEUTIC APPLICATIONS AND APPLICATIONS TO ASSAYS OF METABOLITIES OF VITAMIN D

The present invention relates to new vitamin D derivatives, to a method for preparing them, to their therapeutic application and their application as a diagnostic agent, namely the tracers and immunogens obtained using these derivatives, and to the antibodies obtained using these immunogens, as well as to an assay method and kit using these tracers and antibodies.

Vitamin D is a hormone, the precursor of which is synthesized in the skin as an outcome of a photochemical reaction involving UV irradiation. An insufficiency of irradiation may be compensated by an exogenous provision of vitamin $D_3$ (cholecalciferol) or $D_2$ (ergocalciferol).

Vitamin $D_3$ and vitamin $D_2$ correspond to the following formulae

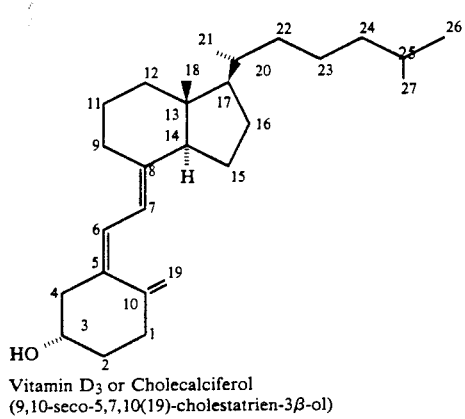

Vitamin $D_3$ or Cholecalciferol
(9,10-seco-5,7,10(19)-cholestatrien-3β-ol)

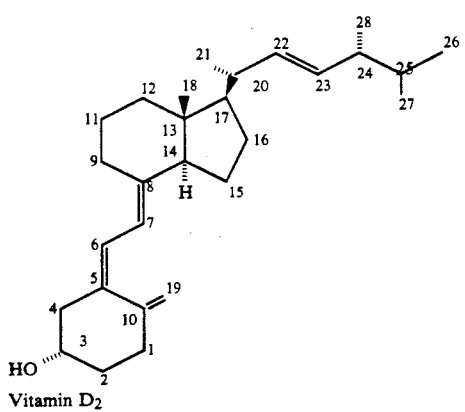

Vitamin $D_2$

Vitamin D undergoes a first hydroxylation in the liver at the 25-position: 25-OH-vitamin D is one of the main forms of circulating vitamin D. This metabolite displays a high affinity for a carrier plasma protein, "vitamin D-binding protein" (DBP), but a low affinity for the intracellular receptor of vitamin D. After hydroxylation at the 1α-position in the kidney, 25-OH-vitamin D is converted to 1α,25-$(OH)_2$-vitamin D, which is the main active metabolite responsible for the biological activity. This metabolite has a low affinity for DBP and a high affinity for the intracellular receptor. Its blood level is regulated within very narrow limits.

The metabolism of vitamin D produces a whole series of other metabolites (for example 24,25-$(OH)_2$-vitamin D; 1,24,25-$(OH)_3$-vitamin D; 25,26-$(OH)_2$-vitamin D, and the like), the physiological role of which, if any, remains poorly defined. An extrarenal production of 1,25-$(OH)_2$-vitamin D is described as occurring in the placenta, and also in keratinocytes and certain hematopoietic cells (monocytes, macrophages), which would explain the excessive production of vitamin D (possibly accompanied by hypercalcemia, hypercalciuria and the consequences thereof) which is observed in some inflammatory states (granulomatous diseases such as sarcoidosis).

At the present time, the pathological conditions associated with vitamin D are classified as vitamin D deficiencies or excesses. Vitamin D deficiencies are due either to insufficient exposure to sunlight combined with an inadequate exogenous provision in the food, or to abnormalities of vitamin D metabolism. Genetic abnormalities are described in respect of the renal hydroxylase (1α-hydroxylase) or in respect of the vitamin D receptor (vitamin D resistance). Interference with the metabolism can also occur in the course of various pathological conditions, and especially renal insufficiency and hypoparathyroidism, or as a result of pharmacological interactions, for example with antiepileptic drugs and corticoids.

The clinical manifestations of these vitamin D deficiencies are most clearly apparent at bone level: rickets, osteomalacia and possibly participation in the phenomena of osteoporosis. There are other, less obvious associated disorders, for example an immune deficiency and a higher incidence of certain cancers and of vascular and endocrine disorders.

Vitamin D excesses are encountered essentially during vitamin D poisoning, or during an ectopic production of active metabolites, for example during granulomatous diseases (sarcoidosis). Hyperparathyroidism stimulates the excessive production of 1,25-$(OH)_2$-vitamin D, which also appears to accompany familial idiopathic hypercalciuria. The active derivatives of vitamin D employed therapeutically, and especially 1,25-$(OH)_2$-vitamin D used, in particular, in renal insufficiency, have a very narrow therapeutic index, so that vitamin poisoning is common during their administration.

Recently, the presence of the vitamin D receptor has been demonstrated in a large number of tissues other than the traditional target tissues (bone, intestine, kidney), and in particular in the skin, breast, colon, brain, endocrine glands, muscle and hematopoietic cells (monocytes, lymphocytes, etc.). A large number of cancer cells of all origins possess vitamin D receptors. 1,25-$(OH)_2$-Vitamin D determines, in these cells, the transition from a state of proliferation to a state of differentiation. It thus behaves as an immunomodulatory substance (for example, stimulation of non-specific immunity by monocytes, inhibition of lymphocytic specific immunity) and regulates the growth and differentiation of normal cells (embryogenesis) and cancer cells (induction of the differentiation of melanoma, breast cancer, myeloid leukemia, lymphoma and osteosarcoma cells, and the like). This might explain the epidemiological observations reporting an immune deficiency in children with rickets, or the higher incidence of cancer of the colon associated with a calcium and vitamin D deficiency, or the prolonged survival of patients with breast cancer in which the vitamin D receptor is expressed.

The usual deficiencies are readily corrected by the exogenous provision of vitamin D. An active form, for example 1,25-(OH)$_2$-vitamin D, must be administered if the metabolism is abnormal: this is, in particular, the case in renal insufficiency. 1,25-(OH)$_2$-Vitamin D has, however, a short half-life, which often justifies the taking of two doses daily. In addition, its therapeutic index is narrow, readily leading to poisoning. The search for derivatives having a different pharmacokinetic profile (for example, through a better affinity for DBP) and a more favorable therapeutic index hence remains ever topical. The administration of an inactive precursor has the advantage of limiting direct activity on the intestine when an oral dose is taken. Some precursors can then be activated by pathways independent of the normal metabolism of vitamin D ("prodrug"). Such derivatives display a special biodistribution, capable of imparting a selectivity of biological effect in vivo. Some are especially well suited to another administration route, such as transcutaneous administration which constitutes, for example, an effective treatment for psoriasis. Finally, some agonists enable the different biological activities with respect to the target cells to be dissociated; thus, derivatives which are active on the differentiation of leukemic cells but have little activity with respect to bone calcium metabolism have been described. These substances have great therapeutic potential (immunomodulation, cancer, atheroma, sugar diabetes, etc.).

There is, as yet, no selective antagonist of vitamin D. Such a product would be useful in many pathological states, in particular vitamin D poisoning, hypercalcemia (neoplastic, hyperparathyroidism, etc.), hypercalciuria (with or without renal lithiases), Paget's disease, granulomatous diseases (sarcoidosis), and the like. According to their spectrum of activity, their biodistribution and the like, antagonists could be combined with agonists in order to obtain a preferential activity in vivo.

The vitamins are hydroxylated in the liver and kidneys and produce a series of metabolites, in particular 25-hydroxyvitamin D, 24,25-dihydroxyvitamin D and 1α,25-dihydroxyvitamin D. These derivatives, and synthetic derivatives such as 1α-hydroxyvitamin D and 1α,24-dihydroxyvitamin D, are also used as a drug in the treatment of certain conditions such as hypoparathyroidism, renal insufficiency and osteoporosis. The very small amounts of these metabolites present or administered in the body require assays possessing high sensitivity in order to follow the variations in these amounts.

Assays for these metabolites necessitate the preparation of derivatives of the latter, for the purpose of labeling them, in particular with a radioactive or enzyme label, in order to obtain a tracer on the one hand, and of coupling them to an immunogenic carrier protein for the production of antimetabolite antibodies on the other hand, in the case of an immunoassay.

However, generally speaking, assays for these metabolites necessitate the use of a ligand having affinity and specific for the metabolite to be assayed. Among these ligands, there may be mentioned:
antibodies, as mentioned above, when the assay is an immunoassay, but also for non-immunological assays, the plasma transporter of vitamin D (vitamin D-binding protein, DBP), or alternatively
the intracellular receptor for vitamin D.

Various derivatives of metabolites of vitamin D intended for an application for immunoassays, in particular as a hapten, have already been proposed in the prior art.

The haptens proposed in Patent Applications FR 2,376,863 and FR 2,376,864 do not enable reagents, in particular antibodies, giving sufficiently sensitive and specific immunoassays of metabolites of vitamin D$_3$ to be obtained.

These haptens have, in effect, the 3- or 25-positions of vitamin D$_3$ occupied by a hemisuccinate group. The antibodies developed by inoculation in animals of the antigens resulting from the coupling of these haptens with an immunogenic carrier protein do not display recognition of the hydroxyl group at the 3- and/or 25-position which can be present on metabolites of vitamin D$_3$.

A branch at the 3-position also affects the recognition of the hydroxyl group at the 1-position of vitamin D$_3$, as a result of their excessively great proximity and the steric hindrance which can result therefrom.

Similarly, a branch at the 25-position affects the recognition of metabolites of the 24-hydroxy- or 1,24-dihydroxyvitamin D$_3$ type.

To remedy these problems, a branch at the 22-position of vitamin D$_3$, with a carboxyl group or its alkyl ester with a chain of 1 to 6 carbon atoms substituted with a carboxyl or amine group, has been proposed in European Patent Application EP 92,004.

However, these haptens are not entirely satisfactory, inasmuch as the 22-position of branching is still in proximity to the 24- and 25-positions where hydroxyl groups specific for recognition of several metabolites of vitamin D$_3$ are bound.

These problems of steric hindrance arise in the same way for the production of radioactive (I-125) or enzyme-labeled tracers, which require chemical branches identical to those described above. Consequently, the branches already described do not enable such tracers to be obtained.

The present invention proposes new vitamin D derivatives possessing a branch at the 11-position, these derivatives being useful as drugs and also for preparing radioisotopic or enzyme-labeled tracers for assays of metabolites of vitamin D including those having a hydroxyl group at the 1-, 24,25- or 26-position, and as haptens for the purpose of preparing immunogens and hence antibodies in the case of immunoassays.

The subject of the present invention is hence vitamin D derivatives corresponding to the following formula I

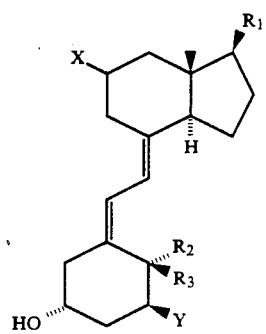

in which
R$_1$ denotes a substituted alkyl group having 1 to 15 carbon atoms, in particular the side chains of vitamin $D_2$ ($C^{20}$ to $C^{28}$) or $D_3$ ($C^{20}$ to $C^{27}$), or these same chains partially modified, in particular hydroxylated at one or more positions, for example the 24-, 25- and/or 26-positions, and/or methylated or ethylated at one or more positions, for example the 24-, 26- and/or 27-positions, and/or halogenated or polyhalogenated at one or more positions, for example perfluorinated (trifluoromethyl) at the 26- and 27-positions, or difluorinated at the 24-position, and/or by the addition of one or more carbon atoms, in particular an atom $C^{24'}$ between the 24- and 25-positions, with the same possibilities of substitution as mentioned above, and/or esterified on one or more hydroxyl groups mentioned above, and/or etherified on one or more hydroxyl groups mentioned above, and/or by replacing one or more carbon atoms by an oxygen, nitrogen or sulfur atom, for example an oxygen at the 22-, 23- or 24-positions, and/or cyclized between carbons $C^{26}$ and $C^{27}$ by a direct bond (cyclopropane) or via a chain of 1 to 3 carbon atoms; it being possible for each of these atoms to bear all the groups or modifications described above, and/or substituted at one or more positions with a saturated, unsaturated, aromatic or heteroaromatic ring, capable of bearing all the groups and modifications described above, and/or unsaturated, with one or more carbon-carbon double or triple bond(s); it being possible for these unsaturated alkyl groups to bear all the groups and modifications described above, and the isomeric forms of the different groups situated on the chain;

Y denotes H or OH or groups derived from the latter such as ester and ether;

X denotes an alkyl chain, in particular of 1 to 6 carbon atoms, optionally substituted at different points by one or more functional group(s) Z, which can be, in particular, a halogen (such as fluorine), a hydroxyl, formyl, carboxyl, amine, thiol, cyano, nitro, sulfoxide, sulfone or phosphono group, or alternatively groups derived from these latter, such as ether, ester, acetal, amide, hydrazine, phosphate or bis(phosphate), or an unsaturated alkyl chain having one or more carbon-carbon double or triple bond(s), it being possible for these chains, in addition, to bear functional groups Z mentioned above, or an aromatic or heteroaromatic ring, optionally substituted with halogens, one (or more) hydroxyl, amine, formyl, carboxyl, thiol, cyano or nitro group(s), or alternatively groups derived from these latter, such as ether, ester, acetal or amide, or a halogen, a cyano, sulfoxide, sulfone, hydroxyl, thiol or amine group, or alternatively derivatives of these latter, such as ether, ester, amine and hydrazine;

$R_2$ denotes a methyl group and $R_3$ an H, or $R_2$ is H and $R_3$ is methyl, or $R_2$ and $R_3$ are H, or alternatively $R_2$ and $R_3$ together denote a methylene group$=CH_2$.

For $R_1$ in the formula I, there may be mentioned, in particular, the following side chains, which are described in the literature (Ref. 2).

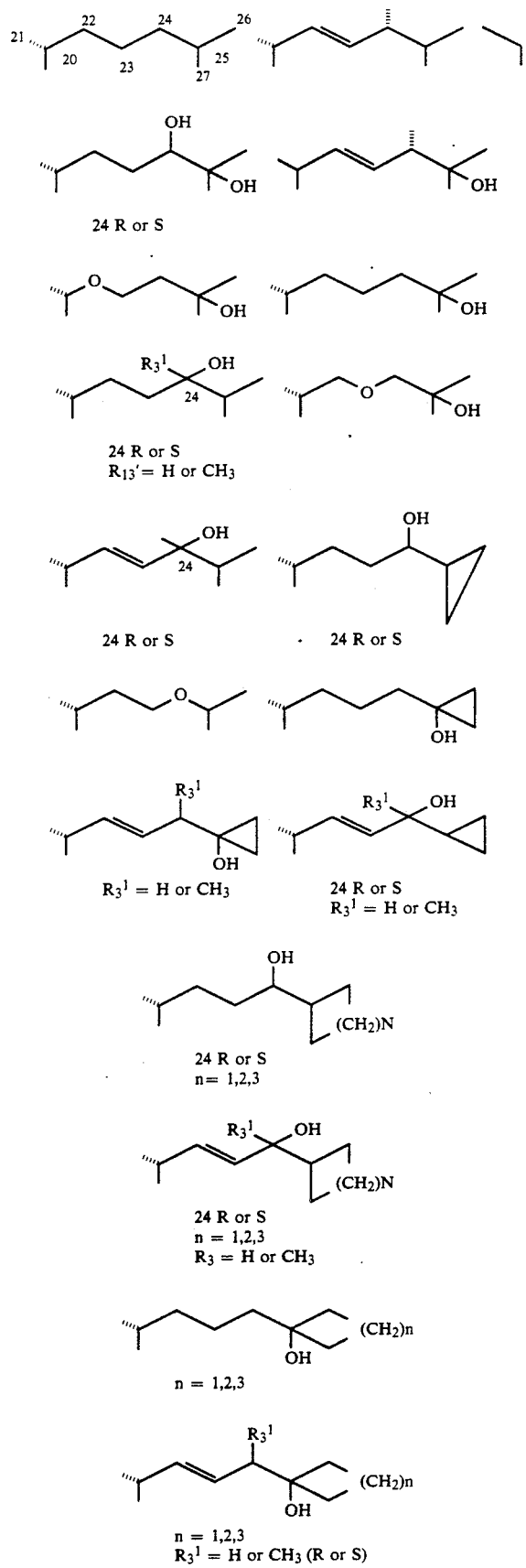

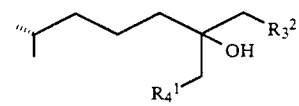

$R_3^2 = H, R_4^1 = CH_3$ (R or S)
$R_3^2 = R_4^1 = CH_3$

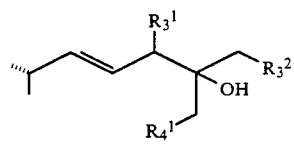

$R_3^2 = H, R_4^1 = CH_3$ (R or S)
$R_3^2 = R_4^1 = CH_3$
$R_3^1 = H$ or $CH_3$ (R or S)

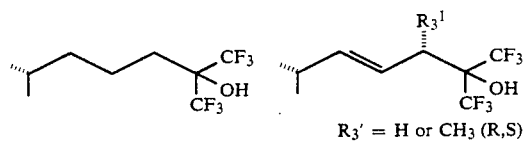

$R_3' = H$ or $CH_3$ (R,S)

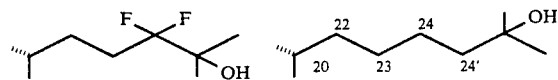

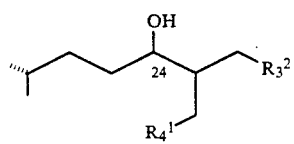

$R_3^2 = H, R_4^1 = CH_3$ (R or S)
24 R or S

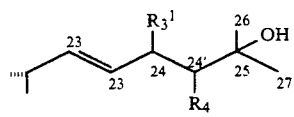

$R_3^1 = R_4^2 = H$
$R_3^1 = CH_3$ (R or S), $R_4^2 = H$
$R_3^1 = H$ $R_4^2 = CH_3$ (R or S)

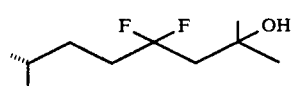

In a particular embodiment, the subject of the present invention is new vitamin $D_3$ derivatives corresponding to the formula I'

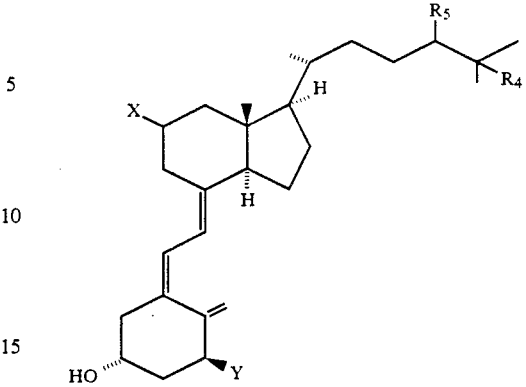

in which

Y, $R_4$ and $R_5$ denote H or OH, in particular (Y, $R_4$, $R_5$) = (H, OH, H), (OH, OH, H), (H, H, OH), (H, OH, OH), (OH, H, OH), (OH, H, H), and X denotes an alkyl chain of 1 to 6 carbon atoms, optionally substituted at its terminal end with a functional group Z which can be, in particular, a hydroxyl, formyl, carboxyl or amine group, or alternatively groups derived from these latter, such as ether, ester, acetal or amide.

Generally speaking, the alkyl chain X can be bound at the 11-position in the α(molecule Iα) or β (molecule Iβ) isomeric form.

In the formulae I and I', the case where the alkyl chain X consists of a methyl, ethyl or phenyl group may be mentioned in particular.

1-, 24- or 25-hydroxy-11-(2-Z-ethyl)vitamin $D_3$ or $D_2$ and 24,25-, 1,24- or 1,25-dihydroxy-11-(2-Z-ethyl)-vitamin $D_3$ or $D_2$ may be mentioned more especially.

As a functional group Z, there may be mentioned, more especially, an -OH group or

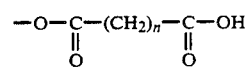

with n between 0 and 10, and preferably n=2.

Derivatives of formula I or I' may be used for preparing the reagents for the purpose of assay of the corresponding metabolite, that is to say possessing the same substituents $R_1$, $R_2$, $R_3$, $R_4$ and $R_5$ and Y.

The subject of the present invention is also a method for preparing a derivative as described above, wherein a derivative of formula II (IIα or IIβ)

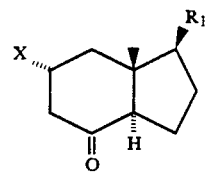

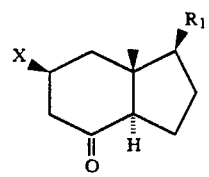

in which X and $R_1$ have the meanings given above, these derivatives being, however, protected, if necessary, on their functional group, is reacted with a derivative of formula III

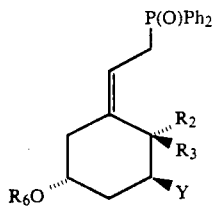

$R_2$ and $R_3$ = $CH_2$
$R_2$ = Me, $R_3$ = H
$R_2$ = H, $R_3$ = Me
Y = H or OR' in which Y, $R_2$ and $R_3$ have the meanings given above, where appropriate being a hydroxyl group protected, in particular, by a group which protects hydroxyl groups, such as dimethyl-t-butylsilyl, and $R_6$ is a group which protects the hydroxyl group, this reaction of the compound of formula II with the compound of formula III being carried out in the presence of n-butyllithium, and the protected groups are then deprotected.

In particular, the subject of the present invention is a method for preparing derivatives of the formula I' above, wherein the reaction is performed of a derivative of formula II' (II'α or II'β)

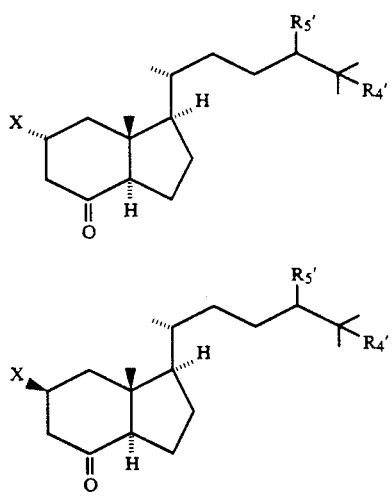

X being protected on its terminal group, with a derivative of formula III'

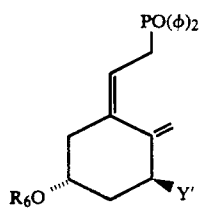

Y', $R'_4$ and $R'_5$ denoting H or a hydroxyl group protected, in particular, by dimethyl ™ t ™ butylsilyl-, and $R_6$ is a group which protects the hydroxyl group.

This reaction of the compound of formula II' with the compound of formula II' with the compound of formula III' is carried out in the presence of n-butyllithium.

Coupling of the keto group of the derivatives of formula II (α and β) with the phosphoryl derivative of formula III is performed according to a method described in the literature (Ref. 3).

The synthesis of the derivatives of formula III has been described in the literature (Ref. 3, Ref. 4).

In a particular embodiment of the method for preparing a protected derivative of formula I, the derivative is prepared with X substituted with a hydroxyl group Z, which is then converted, where appropriate, in particular, to a halogen or a formyl, carboxyl, amine, ester or ether group, such as hemisuccinate, according to methods known to those versed in the art.

The derivative is prepared, in the first place, with its hydroxyl groups protected.

Many examples will be found in the literature of protective groups suitable for the hydroxyl group, in particular in Patent EP 92,004, already mentioned.

There may be mentioned, more especially, according to the present invention, the dimethyl-t-butylsilyl group for the hydroxyl group and for hydroxy groups present in the side chain, and the tetrahydropyranyl group for the hydroxy groups of X.

It is, in effect, possible to introduce changes in respect of the free alcohol before performing deprotection of the protected alcohol groups. This enables derivatives of formula I to be obtained in which X is substituted with groups other than a hydroxyl group. In particular, the aldehyde and corresponding acid may be synthesized by oxidizing the hydroxyl group by a reagent based on chromium VI;

the corresponding amide is obtained by heating the acid or its ammonium salt in the presence of urea;

an amine group may be obtained by reduction of the corresponding amide with $LiAlH_4$;

an ester group may be obtained by esterification of the acid with a suitable alcohol, or of the alcohol with a suitable acid;

an acetal group may be obtained by treating the aldehyde with a suitable alcohol.

A further subject of the present invention is also the compounds of formula

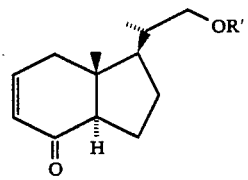

wherein OR'=OH or a derivative group thereof such as ester and ether.

These compounds are especially useful for preparing the vitamin D derivatives of the present invention.

Examples 1 to 17 below detail the Synthesis of the precursors II'α of vitamin D derivatives substituted at the 11α-position from 11-ketoprogesterone.

(Scheme 1)

The derivative of formula II'α may advantageously be prepared according to the method of the invention from 11-ketoprogesterone 1. The compound of formula 1 is subjected to a pyrolysis reaction at approximately 330° C. for 4 hours to give, after conversion of the phenol group to methyl ether in the presence of CH₃I and K₂CO₃, two isomeric diketones 2 and 2'.[5] The derivative 2' may be converted to the desired compound of formula 2, which is thermodynamically more stable, by treatment with sodium hydroxide (NaOH) in methanol. A mixture of 2 and 2' in a 3:1 mole ratio is thereby obtained from pure 2' After this, the isomers are again separated by HPLC. The compound is then converted to the compound of formula 14.

For example, according to Scheme 1, corresponding to the case where X denotes a 2-hydroxyethyl group, the compound 2 is treated with a triethyl phosphonoacetate anion in THF to give the compound 3 in an 80% yield. The compound 3 is then treated with methylenetriphenylphosphorane in THF to give the compound 4. The latter is readily reduced by metal reduction in liquid ammonia in the presence of a proton donor to give the alcohol 5 and corresponding aldehyde, which is also converted to the alcohol with lithium aluminum hydride. The compound 5 is then protected in a conventional manner in the form of an ether, silyl ether or acetal, for example by conversion to the tetrahydropyranyl (THP) ether 6. The compound 6 is then converted to the boron hydride derivative with 9-borabicyclononane (9-BBN) followed by an oxidation of the resulting borane with hydrogen peroxide [6] A single isomer 7 is obtained, in which the stereoisomeric center at C²⁰ formed in this reaction has the desired natural configuration.[6] The hydroxyl of the compound 7 is then converted to a leaving group, for example to the corresponding tosylate 8 with an excess of tosyl chloride at 0° C. in the presence of a catalytic amount of dimethylaminopyridine. To form the chain at C²⁰, use is made of the acetylide in which the hydroxyl group can be protected in the form of an ether, silyl ether or acetal. For example, the acetylide results from the addition of the alkyne 9a to a solution of dimsylsodium.[7] The reaction of 8 with sodium acetylide derived from 9a in excess in DMSO was complete in 1 hour in a 90% yield, to give the compound 10a. The alkyne 10a is then reduced to the derivative 11a by catalytic hydrogenation on 10% Pd/C at a pressure of 4 atmospheres of hydrogen in the presence of triethylamine. Ozonolysis of the aromatic compounds to the corresponding acids 12 is carried out on silica gel at −78° C.[8] In the case where the group R' is deprotected during the ozonolysis, for example in the case of 11c, it is advantageous to reintroduce a protective group such as, for example, a trimethylsilyl ether by treatment with N-(trimethylsilyl)imidazole in dichloromethane. Treatment of the acid 12a with carbonyldiimidazole in THF under irradiaton in a quartz tube for 16 hours at 250 nm gave the mathylene compound 13a[9]. Finally, ozonolysis of 13a at −30° C. to −60° C. in methanol and subjected to Me₂S gives the ketone 14a. As described above, it is advantageous, here too, to reintroduce a protective group R' in the case where deprotection is observed during the ozonolysis, for example of the derivative 13b.

Scheme 1

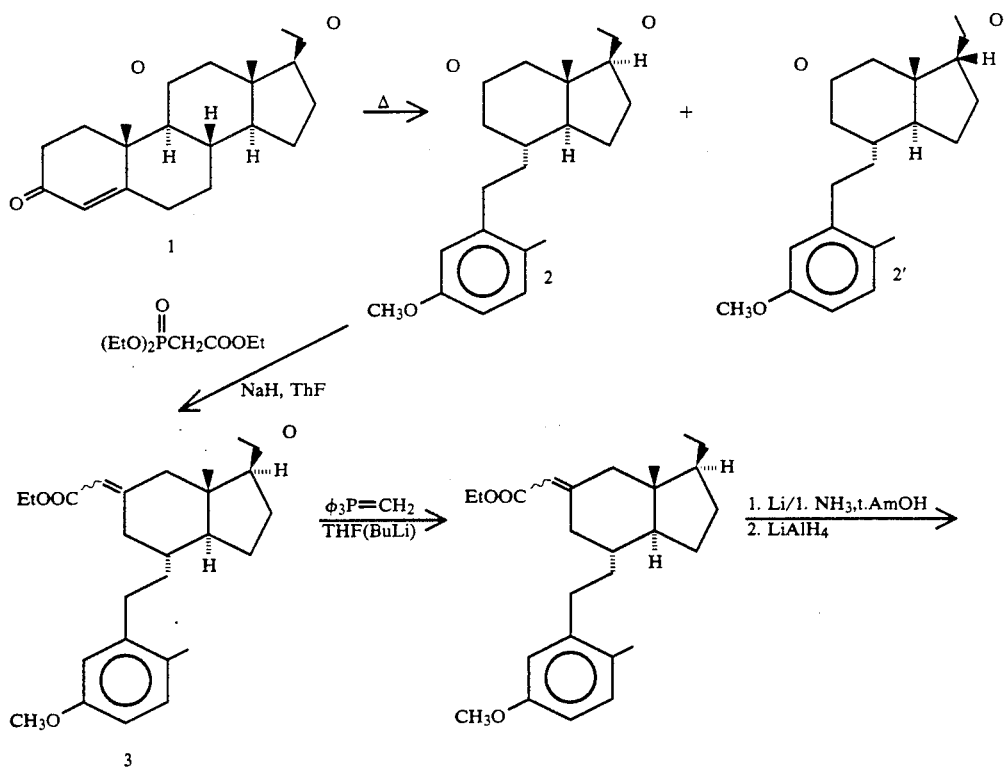

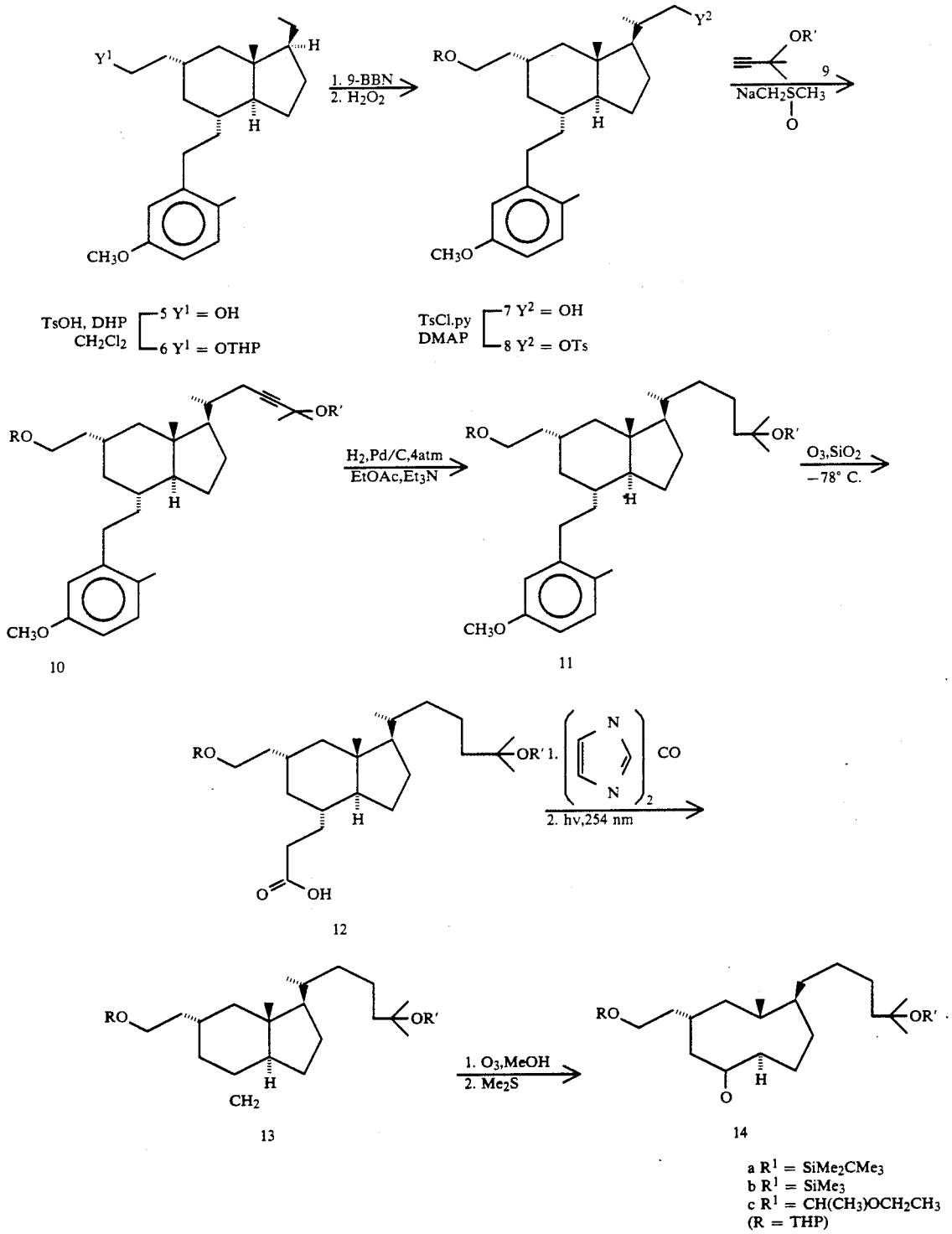

Examples 18 to 32 below detail the Synthesis of the precursors II'α and II'β of vitamin D derivatives substituted at the 11α- and 11β-position, respectively, from vitamin $D_3$ or from vitamin $D_2$ acetate.

(Schemes 2 and 3)

The derivatives of formula II'α and II'β may advantageously be prepared according to the method of the invention from the compound 15. As shown in Scheme 2, the latter compound may be prepared from known alcohols. In particular, treatment of the alcohol 16, obtained from vitamin $D_3$ by ozonolysis followed by reduction with sodium borohydride[10], absorbed on silica gel with ozone at a temperature of −78° C. to 20° C., and subsequent extraction of the silica gel with ethyl acetate followed by chromatographic purification, give the ketone 17 as well as the 25-hydroxylated ketone 18. Similar treatment of the derivative 17 also leads to the ketone 18. Protection of the alcohol in the form of an ether, silyl ether or acetal is carried out according to established methods, for example by conversion to the trimethylsilyl ether 15b or ethoxyethyl (EE) ether 15a. The derivative 15 is also obtained from the diol 19 which, for its part, results from ozonolysis followed by reduction with sodium borohydride of vitamin $D_2$ acetate.[10] As for the formation of the alkyne 10, the derivative 21 is obtained by treatment of the tosylate 20 with the acetylide derived from 9 in DMSO. The tosylate 20 is prepared starting from the alcohol 19, with tosyl chloride in pyridine. Catalytic reduction of the alkyne 21 is performed in ethyl acetate in the presence of triethylamine and palladium under a pressure of 2.8 atmospheres of hydrogen. The alcohol 22 thereby obtained gives, on oxidation, the desired derivative 15. In the case of the compound 22a, the oxidation is advantageously performed by ozonolysis of the product absorbed on silica gel at −78° C., followed by extraction with ethyl acetate.

The introduction of the chain at $C^{11}$ starting with the compound 15 is described in Scheme 3. The ketone is first converted to an α,β-unsaturated ketone 24. Several methods for carrying out this kind of conversion are known in the literature.[11] According to the method of elimination by phenylselenation/oxidation[12], the ketone 15 is treated with lithium diisopropylamide (LDA) in THF at −78° C., followed by an addition of phenylselenyl bromide. Oxidation of the derivative 23 thereby obtained with meta-chloroperbenzoic acid in dichloromethane at −15° C. leads to the desired unsaturated ketone 24. A compound similar to 24 but with a 25:26 double bond has been described.[13] The conjugate addition of the suitable nucleophiles, for example organocuprous reagents[14], cyanide[15] or carbanions of the Michael type[16] can then lead to 11-substituted intermediates. An example is the reaction of the enone 24a with lithium bis(methyl)cuprate in diethyl ether at 0° C., which leads, after purification, to the derivative 25a possessing a methyl group at the 11α-position. Another example is the reaction of the enone 24a with the cuprate obtained from phenyllithium and CuCN in THF[17] at a temperature of −70° C. to −40° C., which leads to the derivative 26a. Yet another example is the reaction of the enone 24b with the lithium cuprate obtained from vinyllithium and CuCN in diethyl ether at −78° C. to −40° C., which leads to the compound 27b. Among other possible derivatives, the last derivative permits the introduction of various groups at $C^{11}$. For example, the reaction of 27b with 9-borabicyclononane (9-BBN) in THF, followed by oxidation of the borane obtained with hydrogen peroxide, gives the alcohol 28b. The latter is protected, for example in the form of the tert-butyldimethylsilyl ether 29b by treatment with tert-butyldimethylsilyl chloride in the presence of imidazole in DMF. Oxidation of the alcohol 29b with pyridinium dichromate in the presence of pyridinium paratoluenesulfonate in dichloromethane gives the compound 30b, analogous to the derivatives 14 described above.

Synthesis of the 11β-substituted ketones IIβ is accomplished using the corresponding 11α-substituted derivatives. The method used consists in introducing a 9:11 double bond which is then reduced by means of catalytic hydrogenation, leading to the 11β isomers. The conversion to the α,β-unsaturated ketone is accomplished as above by phenylselenation/oxidation. For example, the ketone 25a is treated with LDA in THF at −78° C., followed by an addition of phenylselenyl bromide. The expected derivative 31a may also be obtained directly from the enone 24a by treating the intermediate enolate formed in situ by adding lithium bis(methyl)cuprate with phenylselenyl bromide in diethyl ether at −78° C. The phenylselenation/oxidation sequence applied, for example, to the ketone 26a leads to the selenide 32a, and, applied to the ketone 14c, to the selenide 33a. Oxidation of the selenides such as 31, 32 and 33 with meta-chloroperbenzoic acid leads directly to the corresponding enones such as 34, 35 and 36 respectively. Catalytic hydrogenation of these enones is performed in ethyl acetate under 4 atmospheres of hydrogen. The resulting ketones 37, 38 and 39, respectively possess the β stereoisomerism at $C^{11}$.

Scheme 2

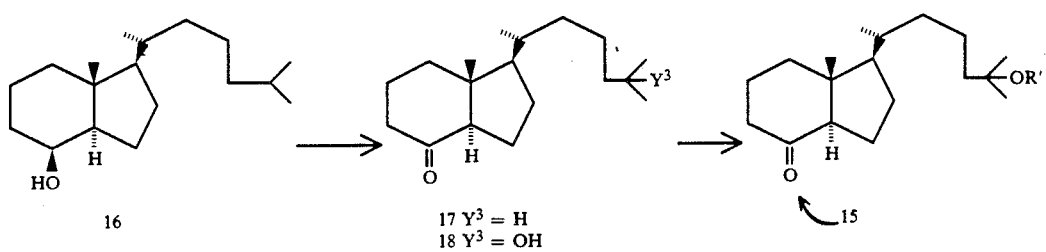

16

17 $Y^3$ = H
18 $Y^3$ = OH

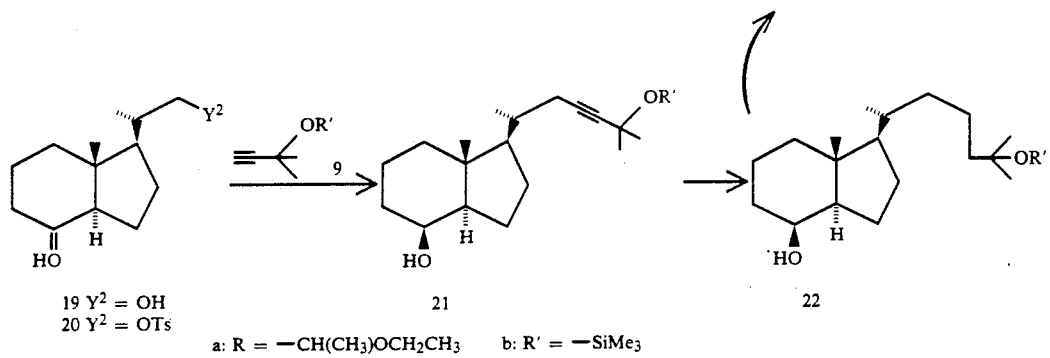
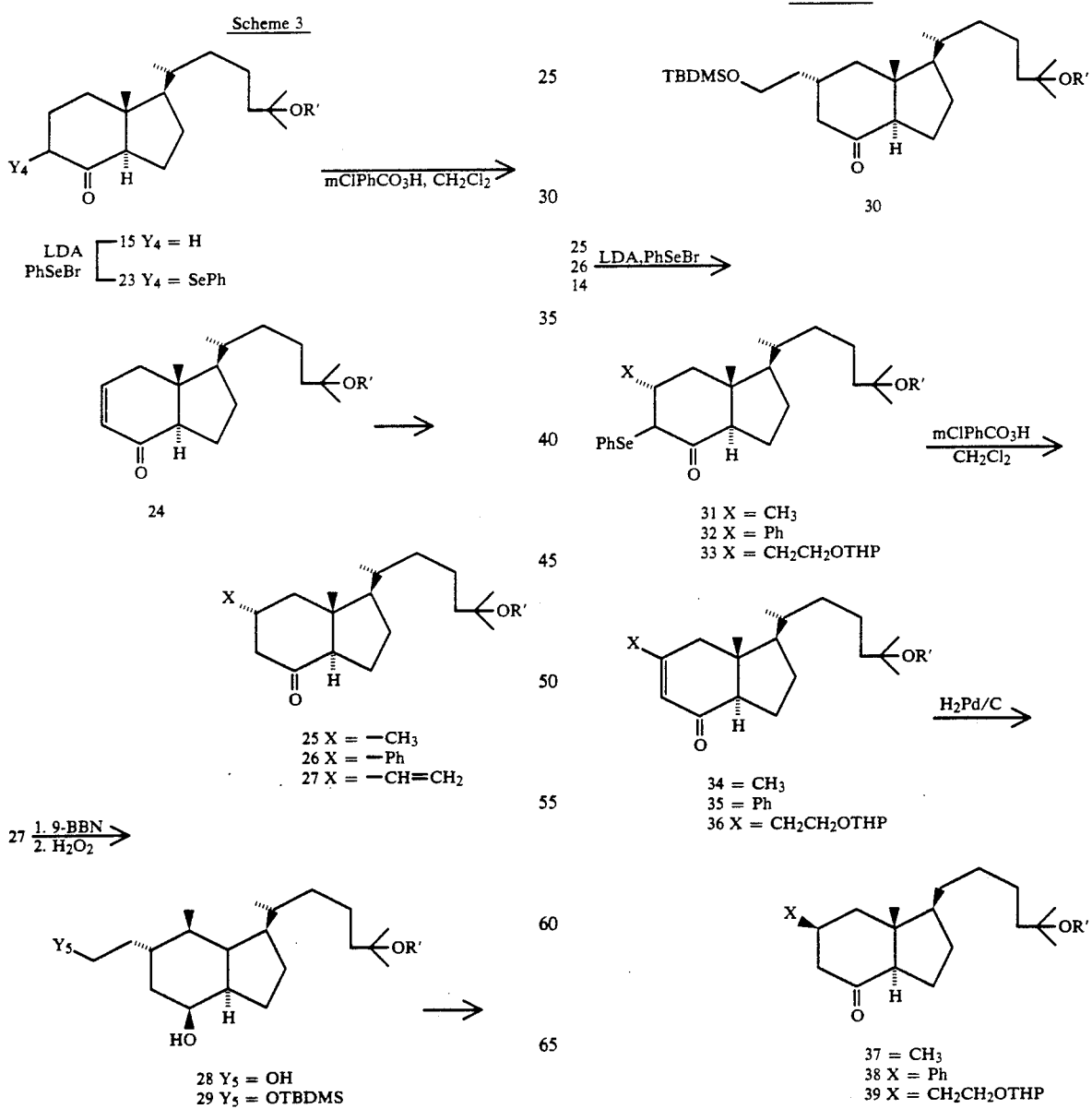

-continued
Scheme 3 a R' = —CH(CH₃)OCH₂CH₃
b R' = —SiMe₃

Examples 33 to 65 below detail the Synthesis of the 11α- and 11β-substituted vitamin D derivatives I by coupling the derivatives II'α and II'β with the derivatives III'.

(Scheme 4)

Coupling of the 11'-substituted ketones such as 14, 26, 26 and 30 with the anion of 40 leads, after purification by chromatography on silica gel, to the protected derivatives such as 41, 42, 43 and 44, respectively. An example is the condensation of the lithium salt, obtained from the phosphonate 40 with n-butyllithium in THF at −78° C., with the ketone 14a, which leads after one and a half hours at −78° C. to the triene 43a. Other examples are the analogous couplings with the ketones 25c and 26c, leading to the trienes 41c and 42c, respectively. Yet another example is the analogous condensation with the ketone 14b leading to the triene 43b, or the ketone 30b leading to the triene 44b. The derivative 43a offers the possibility of a selective deprotection in respect of the THP ether, by treatment with anhydrous magnesium bromide in ether, which gives the alcohol 45a. The reaction of the latter derivative with succinic anhydride in pyridine and in the presence of 4-dimethylaminopyridine leads to the corresponding hemisuccinate 46a.

Removal of the protective groups from the coupling derivatives leads to the production of the triols 47 and 48 starting from 41 and 42, respectively, of the tetrol 49 starting with 43, 44 or 45, or of the acid 50 starting from 46. The hemisuccinate 50 is also advantageously obtained directly by treating the tetrol 49 with succinic anhydride in pyridine in the presence of 4-dimethylaminopyridine.

Coupling of the 11α-substituted ketones II'α with the anion of 51 leads in the same manner to the desired trienes. An example is the condensation of the derivatives 14a, 14b and 30b, leading to the trienes 52a, 52b and 53b, respectively. Here too, hydrolysis of the protective group in the chain at $C^{11}$ may be accomplished selectively and, for example, the alcohol 54a is obtained starting from 52a by treatment with anhydrous magnesium bromide. As before, the hemisuccinate 55 is obtained starting from the alcohol 54. Finally, removal of the protective groups leads to the triol 56 or to the hemisuccinate 57 starting from the derivative 55. It is also advantageous to prepare the hemisuccinate 57 directly from the triol 56.

Coupling of the derivatives II'β with the anion of 40 or 51 is performed in an identical manner. Examples for the case of 40 are included in Scheme 4c.

Examples 66 to 71 below detail the

ALTERNATIVE METHODS

An alternative route (Scheme 5) for the synthesis of type II intermediates can consist in switching the reaction sequence in the sense that the substituent X at the 11-position is introduced before forming the chain at the 17-position. By analogy with the conversion of 24 to 25, 26 or 27 (for example) (Scheme 3, Examples 26, 27, 28), this 1:4-addition to the molecule 66 may be accomplished (R' is a group which protects the hydroxyl group). The compound 66 may be obtained from 20 ($Y^6$ is a group which protects the hydroxyl group) as described for 24 (Scheme 3, Examples 25 and 25a).

As described for the conversion of (for example) 25 to 37 (Examples 30 and 31), the compound 68 may be performed starting from 67. Then, after reduction of the ketone (in 67 and 68, respectively), the side chain is constructed from the group $Y^6$ (as, for example, 20 to 15; Schemes 2 and 3, Examples 21, 22, 23 and 24), thereby leading to the intermediates IIα and IIβ.

An alternative procedure for coupling the intermediates II with the A ring is possible by the method described by L. Castedo and A. Mourino[18] (see Scheme 6). This coupling between 69 and 70 which leads to 71 is accomplished with Pd(PPh₃)₂Cl₂ (3%) and NEt₃ in dimethylformamide at 70° C. Formation of the enol triflates of the type 69 consists in the 1:4-addition to (for example) 24 (see Examples 26, 27 and 28), followed by trapping of the anion of the intermediate enolate with N-phenyltrifluoromethanesulfonimide. An alternative method for the formation of the enol triflates of the intermediates II consists in treating the corresponding ketone (for example 14, 25, 26, 30, 37, 38, 39) with lithium diisopropylamide at between −80° C. and room temperature, followed by addition of N-phenyltrifluoromethanesulfonimide. The compounds 70 (R is a protective group and γ is H or a protected hydroxyl group), precursors of the A ring of vitamin D, have been described in the literature.[13, 19] Selective reduction[20] of the triple bond in 71 is known to lead to the triene system of previtamin D, in equilibrium with the triene system of vitamin D.

Scheme 4a

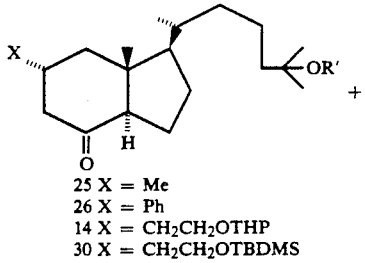

25 X = Me
26 X = Ph
14 X = CH₂CH₂OTHP
30 X = CH₂CH₂OTBDMS

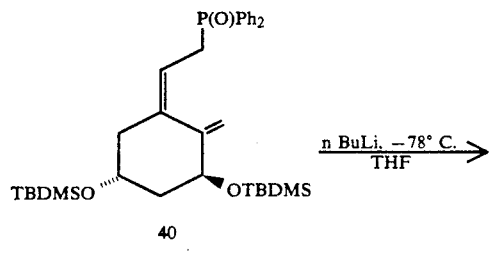

40 n BuLi, −78° C.
THF 5,093,519

Scheme 4a -continued

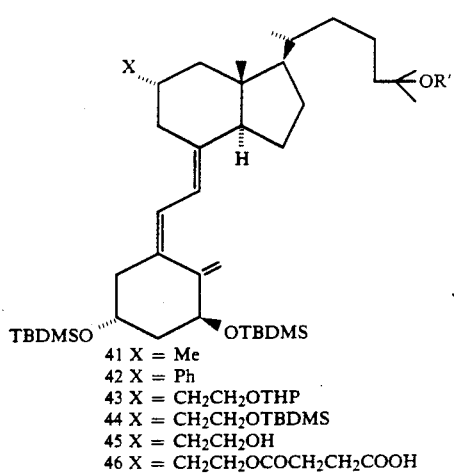

41 X = Me
42 X = Ph
43 X = CH₂CH₂OTHP
44 X = CH₂CH₂OTBDMS
45 X = CH₂CH₂OH
46 X = CH₂CH₂OCOCH₂CH₂COOH

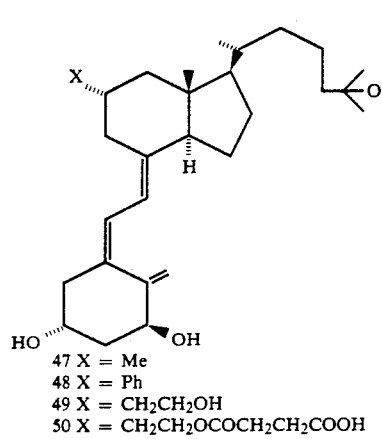

47 X = Me
48 X = Ph
49 X = CH₂CH₂OH
50 X = CH₂CH₂OCOCH₂CH₂COOH a R' = SiC(Me₃)Me₂ (TBDMS)
b R' = SiMe₃
c R' = CH(CH₃)OCH₂CH₃

Scheme 4b

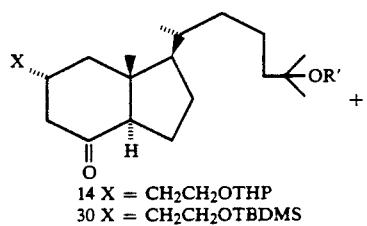

14 X = CH₂CH₂OTHP
30 X = CH₂CH₂OTBDMS

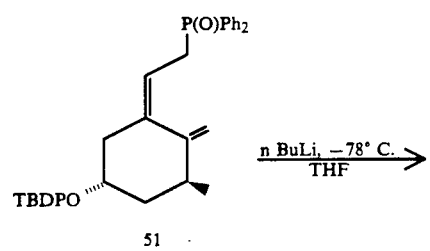

51

Scheme 4b -continued

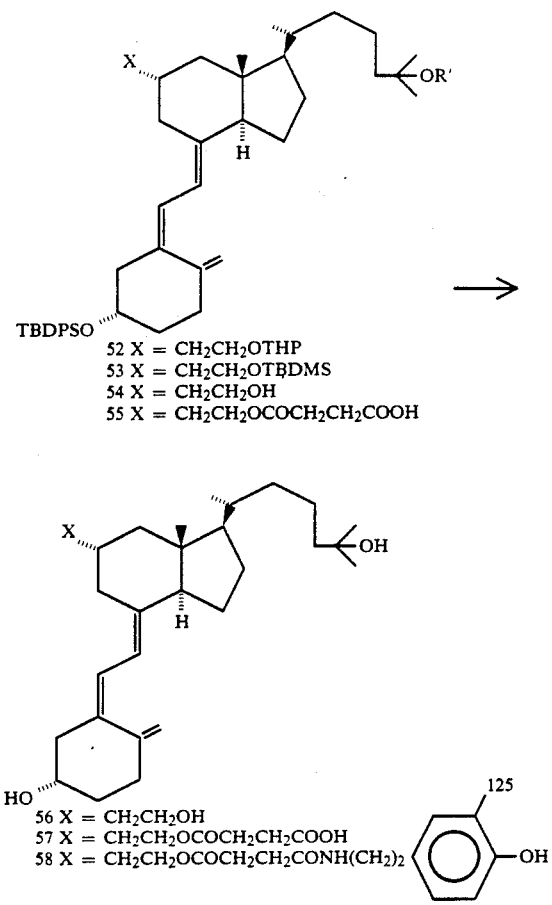

52 X = CH₂CH₂OTHP
53 X = CH₂CH₂OTBDMS
54 X = CH₂CH₂OH
55 X = CH₂CH₂OCOCH₂CH₂COOH

56 X = CH₂CH₂OH
57 X = CH₂CH₂OCOCH₂CH₂COOH
58 X = CH₂CH₂OCOCH₂CH₂CONH(CH₂)₂ —[125I-phenol]—OH a R' = SiC(Me₃)Me₂ (TBDMS)
b R' = SiMe₃
c R' = CH(CH₃)OCH₂CH₃

Scheme 4c

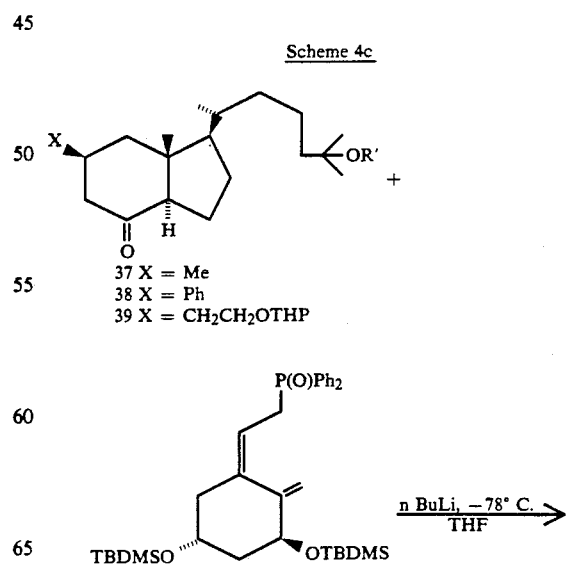

37 X = Me
38 X = Ph
39 X = CH₂CH₂OTHP

40

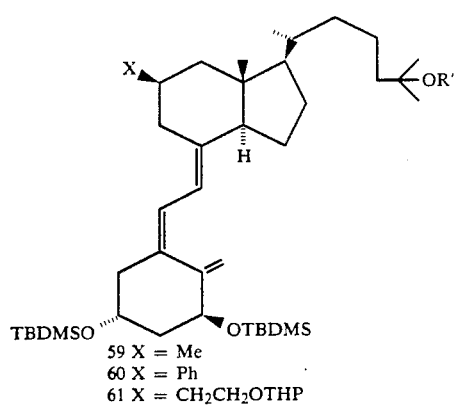
59 X = Me
60 X = Ph
61 X = CH₂CH₂OTHP
62 X = CH₂CH₂OH
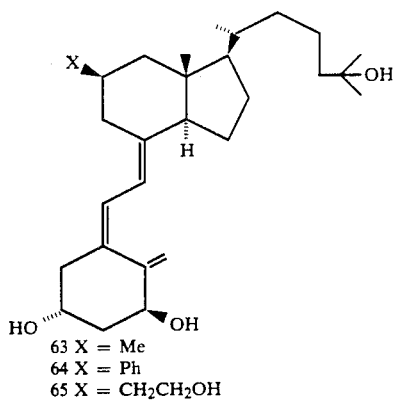
63 X = Me
64 X = Ph
65 X = CH₂CH₂OH
a R' = SiC(Me)₃Me₂ (TBDMS)
b R' = SiMe₃
c R' = CH(CH₃)OCH₂CH₃
Scheme 5
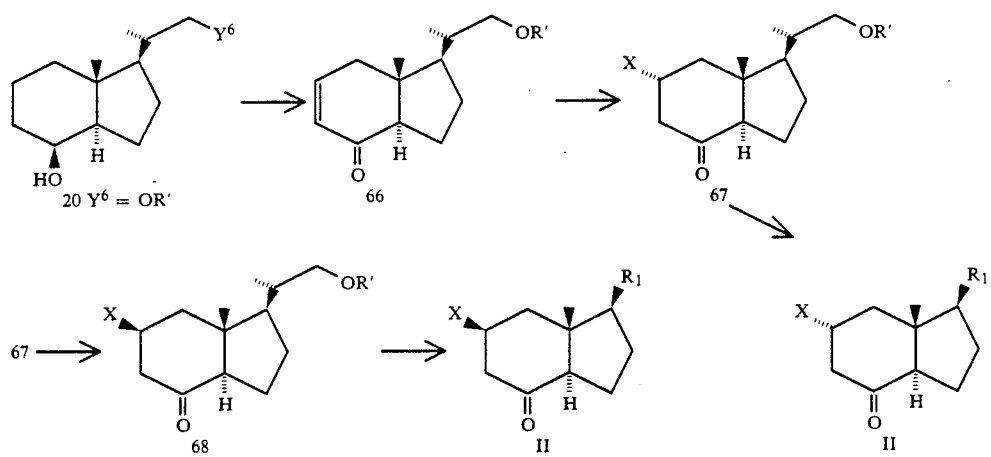
a R' = SiMe₂CMe₃
b R' = CH(CH₃)OCH₂CH₃
Scheme 6
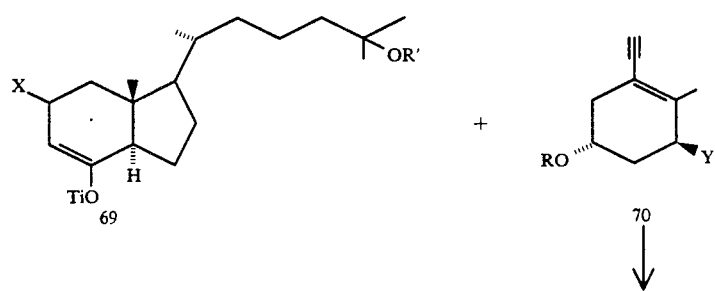

-continued
Scheme 6

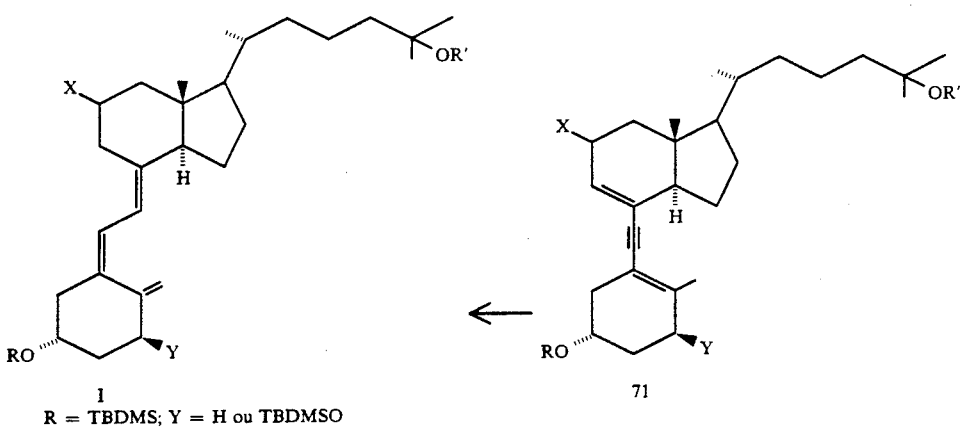

```
1                                71
R = TBDMS; Y = H ou TBDMSO
``` a R' = SiC(Me)₃Me₂ (TBDMS)
b R' = SiMe₃
c R' = CH(CH₃)OCH₂CH₃

The production of the derivatives of formula (I) with X 11-(2-hemisuccinoyloxyethyl) is carried out starting with derivatives with X =11-(2-hydroxyethyl) in a conventional manner using succinic anhydride (for example 45-46, 49-50, 54-55). And, more generally, using an anhydride

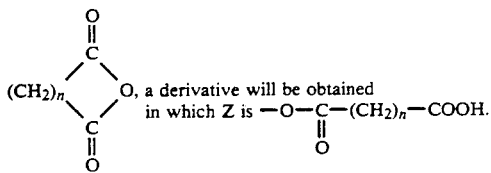

, a derivative will be obtained in which Z is $-O-\overset{O}{\underset{\|}{C}}-(CH_2)_n-COOH$.

It is also possible, starting with 45, 54 or 62, to introduce changes in respect of the free alcohol before performing deprotection of the protected alcohol groups, as mentioned above. This alternative enables derivatives of formula I to be obtained in which X is substituted with groups other than a hydroxyl group. For example:

the hydroxyl group may be converted to a nucleofugic group (for example a tosylate). This permits nucleophilic substitution, introducing groups such as halogens, thiols, ethers, thiolic radicals, amino, cyano, ester, ether;

the corresponding aldehyde or acid may be synthesized by oxidizing the hydroxyl group with a reagent based on chromium VI;

the corresponding amide is obtained by heating the acid or its ammonium salt in the presence of urea;

an amine group may be obtained by reduction of the corresponding amide with LiAlH₄;

an ester group may be obtained by esterification of the acid with a suitable alcohol, or of the alcohol with a suitable acid;

an acetal group may be obtained by treating the aldehyde with a suitable alcohol.

These reactions, well known to those versed in the art, are mentioned purely by way of illustration and hence without implied limitation.

The vitamin D derivatives of formula I, in particular those of vitamin D₃ in particular having a hemisuccinate group at the end of an alkyl branch at the 11-position, are, as mentioned above, useful as a hapten or for obtaining a tracer for the purpose of enzymoimmuno- or radioimmunoassays of metabolites of vitamin D, in particular of vitamin D₃ possessing hydroxyl groups at the 1α-, 24- or 25-position.

When the vitamin D derivatives of formula I are used as a hapten for immunoassays, the said hapten is linked covalently to an immunogenic carrier to form an antigen intended for the preparation of antihapten antibody. The antibody obtained from this antigen yields, where appropriate, one of the reagents which constitute the assay kits according to the invention. The antigens are inoculated into a host animal to induce antibody formation. As a host animal, hot-blooded animals such as rabbits, rats, mice, cattle, sheep, and the like, may be mentioned. The inoculation of an anti9en in a host animal is carried out by extrabuccal administration, for example by means of hypodermic or intradermal injection. The inoculation of the antigen is performed with Freund's complete adjuvant. The inoculation is performed by the injection of, for example, 200 µg of the same antigen hypodermically or intradermally at four-week intervals. During the inoculation period, the antibody concentration in the blood is determined every 10 days, and the whole blood is withdrawn when the largest titer is obtained. The serum, separated from the blood thereby obtained, may be used as an antibody without any treatment, or the immunoglobulins contained therein may be purified beforehand.

As an immunogenic carrier, proteins, polypeptides or glycoproteins, in particular, may be mentioned.

As an example of immunogenic carriers, there may be mentioned, in particular, serum albumin, human serum albumin, methylated bovine serum albumin, rabbit serum albumin, human gamma-globulins, bovine gamma-globulins, polylysine, poly-L-lysine/polyglutamate copolymer, hemocyanins, bovine thyroglobulin, tuberculin and its derivatives, and the like.

The present invention enables an antigen to be obtained in which the derivative of formula I is linked to the immunogenic carrier, for example through an amine or carboxyl group situated terminally on the alkyl chain (X).

The coupling of the derivative of formula I to the immunogenic carrier is obtained by the formation of a covalent link, formed directly or indirectly between a group Z (for example amine or carboxyl) of the alkyl chain (X) of the derivative of formula I and a functional group of the immunogenic carrier. As a functional group of the immunogenic carrier, the amine group of lysine, the carboxyl group of aspartic or glutamic acid, the hydroxyphenyl group of tyrosine and the thiol group of cysteine may be mentioned, for example.

As methods for coupling by covalent bonding, those may be mentioned in which the carboxyl or amine group of X of the derivative of formula I is activated by N-hydroxysuccinimide or an alkyl chloroformate, this being prior to the formation of a covalent link with the immunogenic carrier.

When a derivative of formula I is used as a radioactive tracer in a radioassay, the said derivative is radioiodinated directly with iodine-125 or alternatively coupled to a molecule previously radioiodinated with iodine-125. Among these radioiodinated molecules, molecules possessing an amine group such as [$^{125}$I]tyramine or [$^{125}$I]histamine may be mentioned. The coupling of a derivative of formula I to a radioiodinated molecule is obtained by the formation of a covalent link, formed between a group Z (for example carboxyl) of X of the derivative of formula I and the amine group of the radioiodinated molecule. As a method for the covalent coupling of a radioiodinated molecule to the derivative of formula I, that may be mentioned in which the carboxyl group of the derivative of formula I is activated beforehand in the presence of N-hydroxysuccinimide and dicyclohexylcarbodiimide. The activated derivative of formula I is then coupled to a radioiodinated molecule bearing an amine group. As a method for preparing radioiodinated molecules, there may be mentioned, inter alia, radioiodination with iodine monochloride, oxidation by chlorinated derivatives such as, for example, chloramine T or Iodogen in the presence of radioactive iodine, enzymatic radioiodination with peroxidases and conjugation to radioactive derivatives having an aromatic structure such as, for example, the Bolton-Hunter reagent.

When a derivative of formula I is used as an enzymatic tracer in an immunoassay, the said derivative is coupled covalently to an enzyme. As an enzyme, peroxidases, $\beta$-galactosidase, alkaline phosphatase, glucose oxidase, lipase, luciferases, and the like, may be mentioned, for example. Preferably, horseradish peroxidase (HRP) is used. As a particular method for coupling a derivative of formula I to an enzyme, that described above for the preparation of immunogens may be mentioned. The derivative of formula I (where Z carboxyl) is activated with N-hydroxysuccinimide, this being prior to the formation of a covalent link with the enzyme.

The radioactive (or enzymatic) tracers obtained from the derivatives of formula I may be used as tracers in radioassay (or enzymoassay) methods for metabolites of vitamin D, in particular of vitamin D$_3$ possessing a hydroxyl group at the 1$\alpha$-, 24- and/or 25-position. As radioassays (or enzymoassays), so-called competitive methods may be mentioned, in which the metabolite which it is desired to assay on the one hand, and the tracer on the other hand, compete for a limited number of high affinity binding sites (or ligand). Among methods applicable to the assay of metabolites of vitamin D, there may be mentioned immunoassays (radioimmunoassays, RIA or enzymoimmunoassays, EIA) using antibodies as ligands; receptor assays (radioreceptor assays, RRA or enzymoreceptor assays, ERA) using as ligand the intracellular receptor for vitamin D; or alternatively transporter assays (radiotransporter assays, RTA or enzymotransporter assays, ETA.) with the plasma transporter of vitamin D as ligand.

The subject of the present invention is hence also, generally speaking, assay methods for metabolites of vitamin D, using tracers resulting from the conjugation of a derivative of formula I according to the invention with a labeling component, in particular an enzyme or an iodinated molecule, or antibodies prepared from an antigen consisting of the covalent binding of a vitamin D derivative according to the invention with an immunogenic carrier protein.

The subject of the present invention is also the therapeutic application of the derivatives at the C$^{11}$-position of vitamin D according to the invention, by way of a drug or in the form of a pharmaceutical composition containing them.

The general importance of the branch at the C$^{11}$-position as regards the biological activity of C$^{11}$-derivatives of vitamin D is as follows.

Existing analogs of vitamin D are essentially derivatives formed at the side chain (C$^1$–C$^{27}$) or, to a lesser extent, on the A ring (C$^1$–C$^{10}$).

Various aspects of the relationships between structure and activity are hence now known in relation to the side chain. Some information is also available in respect of the A ring, where the presence of the hydroxyl group at the 1$\alpha$-position, and to a lesser extent at the 3$\beta$-position, is decisive for the biological activity of vitamin D.

There is, in contrast, very little information regarding the remainder of the molecule and, in particular, none concerning the C ring. In particular, no derivative at the C$^{11}$-position has yet been described. This position is especially advantageous on account of its "median" situation away from the two regions for which a structure-activity relationship has been described (namely the side chain and the 1$\alpha$-position). Derivatives a the 11-position hence offer the possibility of introducing chosen modifications of vitamin D without interfering directly with the important functions already known. Such derivatives provide the molecule with novel pharmacological properties, while permitting combination with useful modifications of the regions already explored. The results presented in the present application show that the C$^{11}$-derivatives can modify pharmacological and biological properties of the molecule, but also that it is possible to obtain C$^{11}$-derivatives which preserve the essential functions of vitamin D.

The C$^{11}$-position is especially advantageous for modulating the biological and pharmacological activity of vitamin D derivatives. Among the derivatives described in this application, some are capable of binding DBP or the intracellular receptor for vitamin D with a high affinity, others not. Some of these C$^{11}$-derivatives are capable of reproducing or antagonizing, wholly or partially, the biological properties of 1,25-(OH)$_2$-vitamin D. The possibility of introducing at the 11$\alpha$- or 11$\beta$-position substitutions which increase or antagonize the activity of 1$\alpha$,25-(OH)$_2$-vitamin D, either overall, or in respect of specific targets (immune, cancer, skin, endocrine, cardiovascular and bone cells, and the like) opens up new prospects for applications. It is obvious that such derivatives have novel pharmacological properties, different from 1,25-(OH)$_2$-vitamin D (pharmacokinetics, biodistribution, metabolism, biological activity), and that they find therapeutic applications in many fields of medicine.

Other features and advantages of the present invention will become apparent in the light of the examples and figures which follow.

LEGENDS TO THE FIGURES

FIG. 1

Binding to purified human DBP of 25-OH-vitamin $D_3$, 1,25-$(OH)_2$-vitamin $D_3$ and some $C^{11}$-derivatives of these molecules, measured by displacement of the binding of the tracer [$^3H$]-25-OH-vitamin $D_3$.

| | |
|---|---|
| O——O | 1,25-$(OH)_2$-vitamin $D_3$ |
| ●- - -● | 11-(2-OH-ethyl)-1,25-$(OH)_2$-vitamin $D_3$ |
| □——□: | 25-OH-vitamin $D_3$ |
| ■- - -■ | 11-(2-OH-ethyl)-25-OH-vitamin $D_3$ |
| △- - - -△: | 11-(2-HS-ethyl)-25-OH-vitamin $D_3$ |

FIG. 2

Binding of 1,25-$(OH)_2$-vitamin D and two $C^{11}$-derivatives to the intracellular receptor for vitamin D, measured by displacement of the binding of the tracer ]$^3H$]-1,25-$(OH)_2$-vitamin $D_3$.

| | |
|---|---|
| O——O: | 1,25-$(OH)_2$-vitamin $D_3$ |
| ●- - -● | 11α-(2-HS-ethyl)-1,25-$(OH)_2$-vitamin $D_3$ |
| △———△: | 11α-(2-OH-ethyl)-1,25-$(OH)_2$-vitamin $D_3$ |

FIG. 3

Biological activity, in a test of differentiation of HL 60 cells in vitro, of 1,25-$(OH)_2$-vitamin $D_3$ (active), 25-OH-vitamin $D_3$ and $C^{11}$-derivatives of these molecules (of low activity).

| | |
|---|---|
| ●———●: | 1,25-$(OH)_2$-vitamin $D_3$ |
| O- - -O | 11-(2-OH-ethyl)-1,25-$(OH)_2$-vitamin $D_3$ |
| ▲ —— ▲ | 25-OH-vitamin $D_3$ |
| △- - -△: | 11-(2-OH-ethyl)-25-OH-vitamin $D_3$ |

FIG. 4

Biological activity, in a test of differentiation of HL 60 cells in vitro, of 1,25-$(OH)_2$-vitamin $D_3$ and two $C^{11}$-derivatives, the methyl derivative (very active) and the phenyl derivative (moderately active).

| | |
|---|---|
| ●———●: | 1,25-$(OH)_2$-vitamin $D_3$ |
| O- - -O | 1α,25-$(OH)_2$-11α-methyl-vitamin $D_3$ |
| △- - -△: | 1α,25-$(OH)_2$-11α-phenylvitamin $D_3$ |

EXAMPLE 1

Synthesis of 2 and 2' from 11-ketoprogesterone 1

(a) A pyrolysis of 11-ketoprogesterone 1 in phenanthrene at 333° C. is carried out for 4 to 5 hours, which gives, after purification by HPLC (45% of ethyl acetate in hexane), a mixture of phenols (ratio 2:1, respectively) in a 30 to 60% yield. The procedure followed is that of Reference 5.

(b) A mixture of the above phenols (11 g), methyl iodide (17 ml) and potassium carbonate (30 g) in acetone (110 ml) is heated under reflux for 16 to 20 hours in a nitrogen atmosphere. The mixture is poured into 300 ml of water and extracted with ether (3×100 ml). The organic phase is dried ($MgSO_4$) and concentrated under vacuum and the residue is purified by HPLC (33% ethyl acetate in hexane), giving the pure isomers 2 and 2' in a combined yield of 85%.

The subsequent isomerization of 2' and 2 is accomplished with sodium hydroxide in methanol. The solution of 2' (5.6 g) and sodium hydroxide (1 g) in methanol (80 ml) is stirred at room temperature for 2 days. The methanol is concentrated under vacuum and the residue is treated with ether. An HPLC purification (33% ethyl acetate in hexane) gives the pure isomers 2 and 2'. After 3 isomerizations, 4.9 g of pure 2 are obtained.

Spectroscopic data for 2;

Infrared: 2945 (s), 1700 (s), 1215 (s), 1005 (s), 880 (1) and 695 (s) $cm^{-1}$; $^1H$ NMR (200 MHz, $CDCl_3$): 7.05 (1H, d, J =9Hz), 6.66 (1H, dd: 9, 2.5 Hz), 6.67 (1H, d: 2.5 Hz), 3.78 (3H, s), 2.21 (3H, s), 2.12 (3H, s) and 0.65 (3H, s) ppm. For 2'; $^1H$ NMR: 7.05 (1H, d), 6.66 (1H, dd), 6.67 (1H, d), 3.78 (3H, s), 2.21 (3H, s), 2.13 (3H, s) and 0.88 (3H, s) ppm.

EXAMPLE 2

Synthesis of 3 from the diketone 2 (Scheme 1)

Triethyl phosphonoacetate (6.82 ml) was added slowly to a 60% suspension of sodium hydride in mineral oil (1.38 g), washed with hexane, in tetrahydrofuran (34 ml). The clear solution was then transferred to a solution of diketone 2 (2.34 g) in tetrahydrofuran (10 ml) and the resulting reaction mixture was stirred at room temperature for 12 hours. The mixture was then poured into saturated ammonium chloride solution. After extraction with ether, the organic phase was dried ($MgSO_4$) and purified by column chromatography on silica gel (eluent: 20% ethyl acetate in hexane), to give 2.27 g of 3 (80% yield) in the form of a 1:1 mixture of E and Z isomers.

Spectroscopic data for 3; infrared: 2935 (br, s), 1720, 1705 (s), 1640, 1610 (s), 1500 (s), 1455 (s), 1300–1200 (br, s), 1150 (br, s), 1035 (s) $cm^{-1}$; $^1H$ NMR 7.0 (1H, d: 8 Hz), 6.68 (1H, dd: 8, 2.5 Hz), 6.63 (1H, d: 2.5 Hz), 5.80 and 5.68 (1H, m), 3.77 (3H, s), 2.23 and 2.21 (3H, s), 2.13 and 2.04 (3H, s), 1.29 and 1.28 (3H, t), 0.57 and 0.55 (3H, s) ppm.

EXAMPLE 3

Synthesis of the olefin 4 from the ketone 3 (Scheme 1)

A solution of n-butyllithium in hexane (9.3 ml of a 1.4 M solution) was added (dropwise) at −5° C. to a suspension of methyltriphenylphosphonium bromide (4.7 g) in tetrahydrofuran (20 ml). After 15 minutes, the yellow suspension was brought to room temperature and treated dropwise with a solution of ketone 3 (1.8 g)

in tetrahydrofuran (10 ml). After 10 minutes, the mixture was diluted with saturated ammonium chloride solution. After extraction with hexane (150 ml) and ether (50 ml), the organic phase was washed with water and with brine and then concentrated under vacuum. After the addition of hexane to the residue, the resulting suspension was filtered and the residue obtained after filtration and concentration under vacuum was purified by column chromatography on silica gel (20% ethyl acetate in hexane), to give 1.3 g of olefin 4 (72% yield).

Spectroscopic data; $^1$H NMR (200 MHz, CDCl$_3$): 7.00 and 7.04 (1H, d: 8 Hz), 6.69 (1H, m), 6.63 (1H, m), 5.77 and 5.64 (1H, m), 4.91 (1H, m), 4.76 and 4.73 (1H, m), 3.76 (3H, s), 2.24 and 2.23 (3H, s), 1.83 and 1.76 (3H, s), 1.29 and 1.27 (3H, t), 0.53 and 0.51 (3H, s) ppm.

EXAMPLE 4

Reduction of the olefin 4 to the alcohol 5 (Scheme 1)

Lithium (175 mg) in the form of small pieces of lithium wire) is added to a solution of olefin 4 (1.56 g) in tert-amyl alcohol (1.67 ml) anhydrous tetrahydrofuran (24 ml) and liquid ammonia (50 ml, distilled from sodium). Isoprene (0.5 ml) is added as long as the blue color lasts (15 sec). The ammonia is evaporated off and water and ether are added to the residue. After extraction with ether, the crude residue obtained after concentration under vacuum is then reduced according to the conventional method with lithium aluminum hydride in tetrahydrofuran to give, after purification by HPLC with 20% ethyl acetate in hexane, the desired alcohol 5 (85% yield).

Spectroscopic data: $^1$H NMR (200 MHz, CDCl$_3$): 7.04 (1H, d: 8 Hz), 6.70 (1H, d: 2.5 Hz), 6.65 (1H, dd: 8, 2.5 Hz), 4.87 (1H, m), 4.72 (1H, m), 3.77 (3H, s), 3.72 (2H, t: 7 Hz), 2.23 (3H, s), 1.77 (3H, s), 0.63 (3H, s) ppm.

EXAMPLE 5

Protection of the alcohol 5 as the ether derivative 6 (Scheme 1)

A solution of alcohol (9.5 g), dihydropyran (9.5 ml) and para-toluenesulfonic acid (100 mg) in benzene (150 ml) is stirred for 1 hour at room temperature. The suspension is diluted with triethylamine (2 ml) and filtered on Florisil (20 g) with ether (300 ml). After concentration under vacuum, the residue is purified by HPLC (5% ethyl acetate in hexane), to give 9 g of pure ether 6 (76% yield).

Spectroscopic data; IR: 2935 (s), 1640, 1610, 1580, 1500 (s), 1255 (s), 1035 (s), 800 (s) cm$^{-1}$; MS: mz at 454 (M+, 3), 136 (85), 135 (76), 85 (100); $^1$H NMR (200 MHz, CDCl$_3$): 7.03 (1H, d), 6.71 (1H, d), 6.65 (1H, dd), 4.85 (1H, m), 4.72 (1H, m), 4.60 (1H, m), 3.79 (3H, s), 2.22 (3H, s), 1.78 (3H, s), 0.62 (3H, s) ppm.

EXAMPLE 6

Conversion of the olefin 6 to the alcohol 7 (Scheme 1)

A solution of 9-borobicyclo[3.3.1]nonane in tetrahydrofuran (159 ml of a 0.5 M solution) was added to a solution of olefin 6 (9 g) in anhydrous tetrahydrofuran (140 ml). After stirring for 3 hours at room temperature under an argon atmosphere, a 15% sodium hydroxide solution (34.5 ml) was added at 0° C., followed by water (29 ml). While the temperature was maintained below 15° C., hydrogen peroxide (69 ml of a 27% solution) was added and the resulting solution was stirred at room temperature for 12 hours. The mixture was poured into aqueous sodium sulphite solution (55 g). After extraction with ether, the organic phase was dried (Na$_2$SO$_4$) and concentrated under vacuum and the residue was purified by HPLC with 40% ethyl acetate in hexane as eluent, to give 8.7 g of alcohol 7 (90% yield).

Spectroscopic data; IR: 3630-3100 (br), 2935 (s), 1255 (s), 1030 (s), 800 (s), 735 (s) cm$^{-1}$; MS: m/z at 267 (9), 207 (16), 127 (24), 109 (27), 95 (27), 85 (22), 83 (27), 81 (43), 71 (59), 41 (100); $^1$H NMR (200 MHz, CDCl$_3$): 7.04 (1H, d), 6.65 (1H, dd), 6.70 (1H, d), 4.60 (1H, m), 3.79 (3H, s), 2.22 (3H, s), 1.07 (3H, d), 0.72 (3H, s) ppm.

EXAMPLE 7

Synthesis of the tosylate 8 (Scheme 1)

para-Toluenesulfonyl chloride (5 g) was added at −5° C. to a solution of the alcohol 7 (6.1 g) and dimethylaminopyridine (200 mg) in pyridine (40 ml). Aft mixture was stirred for 3 hours, ice (5 g) was added and the resulting mixture was stirred for 30 minutes. After extraction with ether, the organic phase was washed with brine (2×15 ml), saturated with CuSO$_4$ (3×100 ml), brine (1×15 ml) and saturated with NaHCO$_3$ (1×15 ml). After drying (Na$_2$SO$_4$), the organic phase was concentrated under vacuum and the residue purified by HPLC (eluent: 17% ethyl acetate in hexane), to give 6.5 g of tosylate 8 (80% yield).

Spectroscopic d by HPLC (elue(s), 1610, 1600, 1580, 1500, 1465, 1360 (s), 1180 (s), 1035 (s) cm$^{-1}$; $^1$H NMR (200 MHz, CDCl$_3$): 7.80 (2H, d), 7.35 (2H, d), 7.03 (1H, d), 6.69 (1H, d), 6.65 (1H, dd), 4.60 (1H, m), 3.79 (3H, s), 2.46 (3H, s), 2.21 (3H, s), 1.01 (3H, d), 0.67 (3H, s) ppm.

EXAMPLE 8

Synthesis of the acetylene 10a (Scheme 1)

A suspension of sodium hydride (60% in mineral oil; 3.3 g; washed with 25 ml of pentane) in dimethyl sulfoxide (32 ml) is heated to 70° C. for 2 hours under nitrogen. After the addition of 1-(tert-butyldimethylsilyloxy)-1,1-dimethyl-2-acetylene (9a) (25.8 ml) at room temperature, a solution of tosylate 8 (5 g) in dimethyl sulfoxide (32 ml) is added to the reaction mixture for 30 minutes. After being stirred for 1 hour, the mixture is poured into water (500 ml) and extracted with ether/pentane (5×). The organic phase is washed with saturated NaHCO$_3$ solution, dried (Na$_2$SO$_4$) and concentrated under vacuum. After purification of the residue by HPLC (eluent: 6% ethyl acetate in hexane), 4.6 g of pure acetylene 10a is obtained (87% yield).

Spectroscopic data; IR: 2940, 2240, 1615, 1504, 1470, 1255, 1163 and 940 cm$^{-1}$, $^1$H NMR (200 MHz), CDCl$_3$) 7.02 (1H, d; 8Hz), 6.69 (1H, d), 6.63 (1H, dd: 7.2 1Hz), 4.59 (1H, m), 3.85 (2H, m), 3.48 (2H, m), 3.76 (3H, s), 2.20 (3H, s), 1.42 (6H, s), 1.08 (3H, d: 6.5 Hz), 0.84 (9H, s), 0.70 (3H, s), 0.16 (6H, s) ppm.

EXAMPLE 9

Catalytic hydrogenation of 10a (Scheme 1)

A suspension of acetylene 10a (2.4 g) in ethyl acetate (40 ml) and triethylamine (2.3 ml) containing 10% palladium on charcoal (620 mg) is hydrogenated at a pressure of 4 atmospheres for 3 to 4 hours. The mixture is treated with celite (3 g) and then filtered, giving, after concentration under vacuum, the ether 11a in a 95% yield.

Spectroscopic data for 11a; 2930, 1610, 1580, 1500, 1465, 1255 and 1055 cm$^{-1}$; $^1$H NMR (360 MHz, CDCl$_3$): 7.03 (1H, d: 8 Hz), 6.69 (1H, d:<1 Hz, 6.63

(1H, dd: 8, <1 Hz), 4.60 (1H, m), 3.85 (2H, m), 3.48 (2H, m), 3.80 (3H, s), 2.23 (3H, s), 1.23 (6H, s), 0.92 (3H, d: 6 Hz), 0.86 (9H, s), 0.70 (3H, s), 0.05 (6H, s) ppm.

EXAMPLE 10

Synthesis of the acid 12a by oxidation of 11a (Scheme 1)

A solution of 11a (411 mg) in pentane was treated with a silica gel (20 g) 230–400 mesh) and the pentane was removed under vacuum. The anhydrous silica thereby obtained was cooled to −78° C. under a nitrogen atmosphere. Ozone was then passed through at the rate of 12 l/hour for 15 minutes. After the silica had been flushed completely with nitrogen at room temperature, the product was eluted with ethyl acetate. After concentration under vacuum, the residue was purified by chromatography (eluent: 50% ethyl acetate in hexane), giving 173 mg of acid 12a (65% yield).

Spectroscopic data; IR: 3100 (br), 2900, 1715 (s), 1455, 1370, 1355, 1250, 1025, 830, 765 and 680 cm$^{-1}$; $^1$H NMR (200 MHz, CDCl$_3$): 4.59 (1H, m), 3.82 (1H, m), 3.47 (2H, m), 1.18 (6H, s), 0.92 (3H, d: 6Hz), 0.85 (9H, s), 0.68 (3H, s), 0.05 (6H, s) ppm.

EXAMPLE 11

Synthesis of the olefin 13a (Scheme 1)

Carbonyldiimidazole (73 mg) was added under an argon atmosphere to a solution of the acid 12a (173 mg) in tetrahydrofuran (0.8 ml). After 2 hours, the solution was transferred to a quartz photolysis tube and diluted to a volume of 6.6 ml (0.045 M in the substrate). After the apparatus had been purged with argon, the solution was irradiated at 254 nm for 16 hours.

After concentration, the residue was purified by chromatography on silica gel (eluent: 5% ethyl acetate in hexane), to give 51 mg of olefin 13a (32% yield).

Spectroscopic data; IR: 2950, 2850, 1645, 1465, 1380, 1360, 1250, 1030, 935, 735 and 670 cm$^{-1}$; MS: m/z at 520 (M+, 1), 379 (4), 287 (47), 175 (45), 173 (58), 75 (100); $^1$H NMR (360 MHz, CDCl$_3$): 4.74 (1H, d: 2 Hz), 4.47 (1H, d: 2 Hz), 4.58 (1H, m), 3.82 (2H, m), 3.46 (2H, m), 1.18 (6H, s), 0.94 (3H, d: 6.2 Hz), 0.85 (9H, s), 0.56 (3H, s), 0.06 (6H, s), ppm.

EXAMPLE 12

Synthesis of the ketone 14a (Scheme 1)

Ozone was passed through a cooled (−30° C.) solution of olefin 13a (10 mg) in methanol (5 ml) until the solution became blue. After a subsequent cooling to −60° C., the excess ozone was removed by flushing with nitrogen at −60° C. Dimethyl sulfide (200 ml) was added and the mixture was maintained at 0° C for 15 minutes. After stirring at room temperature for a further 12-hour period, the solution was concentrated under vacuum and the residue was purified by chromatography on silica gel (10% ethyl acetate in hexane), to give 7.8 mg of ketone 14a (79% yield).

Spectroscopic data; IR: 3020, 2920, 1720 (s), 1460, 1380, 1360, 1250, 1135, 1120, 1030, 830, 770 cm$^{-1}$; $^1$H NMR (360 MHz, CDCl$_3$): 4.56 (1H, m), 3.82 (2H, m), 3.50 (1H, m), 3.40 (1H, m), 1.18 (3H, s), 1.17 (3H, s), 0.96 (3H, d: 5.8 Hz), 0.85 (9H, s), 0.65 (3H, s), 0.06 (6H, s) ppm.

EXAMPLE 13

Synthesis of the alkyne 10c (Scheme 1)

The synthesis is performed in the same manner as described in Example 8, but using 1-(ethoxyethyloxy)-1,1-dimethyl-2-acetylene 9c.

Spectroscopic data for 10c: $^1$H NMR (360 MHz, CDCl$_3$): 7.03 (1H, d, 8.2 Hz), 6.69 (1H, d, 2.5 Hz), 6.64 (1H, dd, 2.5, 8.2 Hz), 5.12 (1H, q, 5.2 Hz), 4.60 (1H, q, 3.2 Hz), 3.85 (2H, m), 3.77 (3H, s), 3.68 (1H, m), 3.52 (2H, t, 7.1 Hz), 3.47 (1H, m), 2.63 (1H, ddd, 5.0, 13.1, 13.1 Hz), 2.41 (1H, m), 2.25 (1H, m), 2.17 (3H, s), 1.99 (2H, m), 1.51 (3H, s), 1.44 (3H, s), 1.33 (3H, d, 5.2 Hz), 1.19 (3H, t, 7.1 Hz), 1.07 (3H, d, 6.5 Hz), 0.70 (3H, s) ppm.

EXAMPLE 14

Synthesis of the acid 12b (Scheme 1)

The synthesis is accomplished by the oxidation of 11b according to Example 10.

Spectroscopic data for 12b; $^1$H NMR (360 MHz, CDCl$_3$): 4.58 (1H, m), 3.87 (1H, m), 3.77 (1H, m), 3.51 (1H, m), 3.40 (1H, m), 2.40 (1H, m), 2.28 (1H, m), 1.99 (1H, m), 1.21 (6H, s), 0.93 (3H, d, 6.4 Hz), 0.67 (3H, s), and 0.06 (9H, s) ppm.

EXAMPLE 15

Synthesis of the acid 12b (Scheme 1, R =TBDMS)

The synthesis is performed as described in Example 14.

Spectroscopic data: $^1$H NMR (360 MHz, CDCl$_3$): 3.62 (2H, m), 2.32 (2H, m), 1.95 (1H, d, 13 Hz), 1.20 (6H, s), 0.93 (3H, d, 6.5 Hz), 0.90 (9H, s), 0.67 (3H, s), 0.10 (9H, s) and 0.05 (6H, s) ppm.

EXAMPLE 16

Synthesis of the olefin 13b (Scheme 1)

The synthesis is accomplished starting from the acid 12b, as described in Example 11.

Spectroscopic data: $^1$H NMR (360 MHz, CDCl$_3$): 4.74 (1H, s), 4.59 (1H, m), 4.47 (1H, brs), 3.87 (1H, m), 3.79 (1H, m), 3.51 (1H, m), 3.41 (1H, m), 2.35 (1H, m), 2.07 (1H, m), 1.20 (6H, s), 0.94 (3H, d, 6.1 Hz), 0.57 (3H, s), 0.10 (9H, s) ppm.

EXAMPLE 17

Synthesis of the ketone 14b (Scheme 1, R =TBDMS)

A solution of the olefin 13b (R =TBDMS) (85 mg) in a mixture of anhydrous methanol (37 ml), anhydrous dichloromethane (6.8 ml) and anhydrous pyridine (0.68 ml) is cooled to −70° C. and subjected to a stream of ozone at the rate of 10 l/hour for 3 minutes. The excess is then flushed out with nitrogen and dimethyl sulfide (0.08 ml) is added. The solution is brought back to room temperature and, after a further 12-hour period, a phosphate buffer solution (0.5 M, pH 7.0, 50 ml) is added and the mixture is concentrated under vacuum. After extraction of the buffered solution (4 times) with dichloromethane, the combined extracts are filtered on silica gel (35-70 mesh) and the filtrate is concentrated under vacuum. The residue is dissolved in dichloromethane (5 ml) and treated with N-(trimethylsilyl)imidazole (0.3 g). After being stirred for 2 hours, the solution is concentrated under vacuum and the residue is purified by HPLC (n-hexane/ethyl acetate 95:5), to give 63 mg of the ketone 14b (R =TBDMS) (74% yield).

Spectroscopic data: $^1$H NMR (360 MHz, CDCl$_3$): 3.63 (2H, m), 2.30 (4H, m), 1.91 (1H, m), 1.70 (1H, m), 1.19 (6H, s), 0.96 (3H, d, 6.5 Hz), 0.88 (9H, s), 0.63 (3H, s), 0.09 (9H, s), 0.05 (6H, s) ppm.

EXAMPLE 18

Ozonolysis of the alcohol 16 (Scheme 2)

Silica gel (53 g; 230–400 mesh) is added to a solution of the alcohol 16 (8.8 g) in hexane (200 ml) and the mixture is concentrated under vacuum. A suspension of the residue in freon 11 (600 ml) is treated with ozone at −25° C. until a blue color is obtained. The temperature is brought back to 4° C. over a period of 3 hours. This process is repeated. The excess ozone is then flushed out in a stream of nitrogen and the mixture is filtered at −30° C. The oxidation products are then released by extraction of the silica with ethyl acetate (250 ml). After concentration under vacuum, the residue is purified by chromatography on silica gel, eluting with 10 to 50% ether/hexane. 5.053 g of ketone 17 (57% yield) and 658 mg of alcohol 18 (7% yield) are obtained in this manner.

Spectroscopic data for 18; $^1$H NMR (360 MHz, CDCl$_3$): 2.45 (1H, dd: 7.3 and 11.6 Hz), 1.22 (6H, s), 0.97 (3H, d, 6.1 Hz), 0.64 (3H, s) ppm. MS m/z: 280 (M+, 0.6), 279 (M+-1, 1), 262 (21), 247 (9), 178 (12), 229 (2.5), 207 (2.5), 191 (3), 178 (12), 149 (25), 124 (25), 111 (41), 95 (27), 81 (40), 69 (39), 59 (80), 55 (88), 43 (100).

EXAMPLE 19

Derivatization of the alcohol 18 to the trimethylsilyl ether 15b (Scheme 2)

A solution of the alcohol 18 (200 mg) and N-(trimethylsilyl)imidazole (0.714 ml) in dichloromethane (13 ml) is stirred at room temperature for 16 hours. After water (4.9 ml) has been added, the mixture is left stirring for 20 minutes. The mixture is then extracted with ethyl acetate. The organic phases are washed with brine and dried. After concentration under vacuum, the residue is purified by chromatography on silica gel (230–400 mesh) (12% diethyl ether in hexane), to give 200 mg of derivative 15b (80% yield).

Spectroscopic data: MS: m/z at 480 (M+, 1), 465 (3), 422 (3), 396 (2), 378 (1), 351 (1), 337 (7), 321 (3), 306 (4), 293 (2), 267 (2), 261 (1), 250 (1), 241 (2), 227 (1), 193 (1), 173 (1), 155 (2), 143 (2), 131 (100), 85 (48), 73 (36).

EXAMPLE 20

Derivitization of the alcohol 18 to the ethoxyethyl ether 15a (Scheme 2)

Ethoxyethylene (6 ml) and 5 drops of trifluoroacetic acid are added to a solution of the alcohol 18 (515 mg) in dichloromethane (10 ml). The mixture is stirred at room temperature for 24 hours. After the addition of ether, the mixture is washed with sodium bicarbonate and brine. After drying (MgSO$_4$), filtration and concentration under vacuum, the residue is purified by chromatography on silica gel (10% to 50% diethyl ether/hexane), to give 428 mg of ether 15a (66% yield). Rf in 50% ether/hexane: 0.44

Spectroscopic data: $^1$H NMR (500 MHz, CDCl$_3$) 4.86 (1H, k, 5.27 Hz), 3.49 (2H, m), 2.44 (1H, dd, 7.47 Hz, 11.7 Hz), 2.24 (2H, m), 2.12 (1H, m), 1.26 (3H, d, 5.30 Hz), 1.20 (3H, s), 1.18 (3H, s), 1.17 (3H, t, 6.30 Hz), 0.95 (3H, d, 6.14 Hz), 0.63 (3H, s) ppm.

EXAMPLE 21

Synthesis of the tosylate 20 (Scheme 2)

A solution of diol 19 (1.9 g) and para-toluenesulfonyl chloride (2.56 g) in pyridine (38 ml) is kept at 0° C. for 14 hours. After ice has been added, the suspension is extracted with 40% ethyl acetate in hexane. The organic phase is washed with 5% hydrochloric acid, water and saturated bicarbonate. After being dried, it is concentrated under vacuum and the residue is purified on silica gel (50% ethyl ether in hexane), to give 2.831 g of 20 (86% yield).

Rf of 20 in 50% ether/hexane: 0.16

Spectroscopic data: $^1$H NMR (500 MHz, CDCl$_3$) 7.78 (2H, d, 7.76 Hz), 7.34 (2H, d, 8.04 Hz), 4.06 (1H, bs), 3.95 (1H, dd, 2.76 Hz, 9.00 Hz), 3.81 (1H, dd, 6.25 Hz, 9.17 Hz), 2.44 (3H, s), 0.96 (3H, d, 6.61 Hz), 0.89 (3H, s) ppm.

EXAMPLE 22

Synthesis of the alkyne 21a (Scheme 2)

The synthesis is performed in a manner similar to that described in Example 13. Using 2.3 g of sodium hydride (60%; washed with 10 ml of hexane), 26 ml of DMSO, 16 ml of acetylene and 2.372 g of tosylate in 26 ml of DMSO, 1.723 g of alkyne 21a are obtained (76% yield).

Spectroscopic data: $^1$H NMR (500 MHz, CDCl$_3$): 5.12 (1H, k, 5.14 Hz), 4.08 (1H, bs), 3.68 (1H, m), 3.49 (1H, m), 2.24 (1H, dd, 3.47 Hz, 16.6 Hz), 2.03 (1H, dd, 7.56 Hz, 16.6 Hz), 1.98 (1H, m), 1.82 (3H, m), 1.50 (3H, s), 1.43 (3H, s), 1.32 (3H, ad, 5.22 Hz), 1.18 (3H, et, 7.01 Hz), 1.04 (3H, d, 6.56 Hz), 0.94 (3H, s) ppm. MS m/z: 335 (0.07), 306 (1.2), 291 (1.6), 277 (1.2), 259 (2.0), 243 (4.5), 227 (0.92), 217 (1.2), 201 (1.9), 187 (3.4), 173 (2.3), 161 (5.5), 149 (7.6), 135 (9.0), 121 (5.5), 107 (12), 95 (15), 81 (19), 73 (100), 67 (17), 55 (40), 45 (79).

EXAMPLE 23

Synthesis of the alcohol 22a (Scheme 2)

A solution of the alcohol 21a (1.723 g) in ethyl acetate (40 ml) containing triethylamine (2.3 ml) and palladium/C (10%; 620 mg) is treated under pressure of 2.8 atmospheres of hydrogen for a period of 12 hours. After the addition of celite, the solution is filtered and then concentrated under vacuum. The residue thereby obtained is purified on silica gel (15 to 20% ether/hexane), to give 1.573 g of 22a (90% yield).

Rf of 22a in 40% diethyl ether in hexane: 0.31.

Spectroscopic data: $^1$H NMR (500 MHz, CDCl$_3$): 4.86 (1H, k, 5.24 Hz), 4.06 (1H, bs), 3.49 (2H, m), 1.99 (1H, m), 1.81 (3H, m), 1.26 (3H, ad, 5.22 Hz), 1.19 (3H, s), 1.18 (3H, s), 1.17 (3H, t, 6.80 Hz), 0.92 (3H, s), 0.89 (3H, d, 6.40 Hz) ppm.

EXAMPLE 24

Oxidation of the alcohol 22a (Scheme 2)

A suspension of the alcohol 22a (1.4 g) and silica gel (10 g; 230–400 mesh) in hexane (150 ml) is concentrated under vacuum. A suspension of the residue in freon 11 (150 ml) is treated at −78° C. for 15 minutes with ozone until a blue color is achieved. The mixture is then maintained at −78° C. for 2 hours. This process is repeated. After removal of the excess ozone with a stream of nitrogen, the mixture is filtered at −30° C. The oxidation products are eluted with ethyl acetate (150 ml). After concentration under vacuum, the residue is purified by silica gel (10% to 20% diethyl ether/hexane), to give 983 mg of 15a (70% yield).

Spectroscopic data: $^1$H NMR (500 MHz, CDCl$_3$): 4.86 (1H, k, 5.27 Hz), 3.49 (2H, m), 2.44 (1H, dd, 7.47 Hz, 11.7 Hz), 2.24 (2H, m), 2.12 (1H, m), 1.26 (3H, d, 5.30 Hz), 1.20 (3H, s), 1.18 (3H, s), 1.17 (3H, t, 6.30 Hz), 0.95 (3H, d, 6.14 Hz), 0.63 (3H, s) ppm.

EXAMPLE 25

Synthesis of the enone 24a (Scheme 3)

A solution of the ketone 15a (1.587 g) in THF (9 ml) is added dropwise over a period of 10 minutes to a solution containing lithium diisopropylamide, prepared from diisopropylamine (0.833 ml) and n-butyllithium (2.5 ml of a 2.19 M solution in hexane) at −20° C., in THF (9 ml) cooled to −78° C. After stirring at −40° C., a solution of phenylselenyl bromide (1.305 g) in THF (4.5 ml) is added. After the addition of saturated ammonium chloride solution (20 ml) and ether (40 ml), the organic phase is washed with water, saturated bicarbonate and brine, and dried. After concentration under vacuum, the residue is purified on silica gel (10% to 12% diethyl ether/hexane), to give 1.753 g of selenide 23a (77% yield).

A solution of meta-chloroperbenzoic acid (0.773 g) in dichloromethane (30 ml) is added dropwise over a period of 10 minutes to a solution, cooled to −15° C., of the selenide 23a (1.753 g) in dichloromethane (15 ml). The reaction mixture is then poured into saturated sodium bicarbonate solution, which is extracted with ether. The organic phase is washed with brine and dried. After concentration under vacuum, the residue is purified on silica gel (10% to 20% diethyl ether/hexane), to give 0.856 g of enone 24a (71% yield).

Spectroscopic data for 24a: $^1$H NMR (500 MHz, CDCl$_3$): 6.75 (1H, ddd, 2.18 Hz, 5.73 Hz, 9.93 Hz), 5.98 (1H, ddd, 0.75 Hz, 2.71 Hz, 9.93 Hz), 4.86 (1H, k, 5.26 Hz), 3.49 (2H, m), 2.62 (1H, ddd, 0.75 Hz, 5.79 Hz, 18.6 Hz), 2.56 (1H, dd, 8.88 Hz, 10.5 Hz), 2.40 (1H, dt, 2.31 Hz, 18.6 Hz), 1.26 (3H, d, 5.23 Hz), 1.20 (3H, s), 1.18 (3H, s), 1.16 (3H, t, 7.05 Hz), 0.93 (3H, d, 6.42 Hz), 0.73 (3H, s) ppm.

EXAMPLE 25a

Synthesis of the enone 24b (Scheme 3)

This synthesis is performed starting with the ketone 15b, in the same manner as described in Example 25.

Spectroscopic data for 24b: $^1$H NMR (360 MHz, CDCl$_3$): 6.76 (1H, ddd, 2.25 Hz, 5.75 Hz, 9.95 Hz), 5.99 (1H, ddd, 0.93 Hz, 3.1 Hz, 9.93 Hz), 2.64 (1H, ddd, 1.1 Hz, 5.82 Hz, 18.4 Hz), 2.58 (1H, dd, 8.8 Hz, 10.7 Hz), 2.42 (dt, 1H, 2.67 Hz, 18.5 Hz), 1.95 (1H, m), 1.20 §6H, s), 0.95 (3H, d, 6.32 Hz), 0.76 (3H, s), 0.10 (9H, s) ppm.

EXAMPLE 26

Conjugate addition to the enone 24: synthesis of 25a (Scheme 3)

A solution of methyllithium in diethyl ether (0.74 ml of a 1.4 molar solution) is added to a suspension of CuI (0.117 g) in ether (0.5 ml) at 0° C. After stirring at 0° C. for a period of 20 minutes, a solution of the enone 24a (60 mg) in ether (0.5 ml) is added. After being stirred for a further 30 minutes, the reaction mixture is poured into saturated ammonium chloride solution. After extraction with ether, the organic phase is washed with brine and dried. After concentration under vacuum, the residue is purified on silica gel (ether/hexane, 1:9), to give 55 mg of ketone 25a (80% yield).

Spectroscopic data: $^1$H NMR (500 MHz, CDCl$_3$): 4.86 (1H, k, 5.26 Hz), 3.49 (2H, m), 2.41 (1H, dd, 7.42 Hz, 1.7 Hz), 2.30 (1H, dd, 5.34 Hz, 13.4 Hz), 2.16 (1H, m), 2.13 (1H, dd, 3.78 Hz, 12.5 Hz), 1.90 (1H, td, 1.2 Hz, 2.2 Hz), 1.89 (1H, m), 1.69 (1H, m), 1.26 (3H, d, 5.31 Hz), 1.20 (3H, s), 1.18 (3H, s), 1.17 (3H, t, 6.81 Hz), 1.03 (3H, d, 6.27 Hz), 0.95 (3H, d, 5.93 Hz), 0.63 (3H, s) ppm.

MS: m/z: 308 (1), 277 (3), 259 (24), 236 (1.5), 205 (11), 203 (11), 165 (6), 125 (4), 109 (3), 95 (7), 81 (8), 73 (100), 69 (17), 55 (19), 45 (40).

EXAMPLE 27

Conjugate addition to the enone 24; synthesis of 26a (Scheme 3)

A solution of phenyllithium (0.9 ml of a 2 molar solution in cyclohexane/diethyl ether) is added to a suspension of CuCN (81 mg) in THF (1 ml) at −78° C. After 10 minutes, the temperature is brought back to -25° C, and then for 3 minutes to 0° C. The temperature is then brought back to −78° C. and a solution of the enone 24a (53 mg) in THF (1 ml) is added. After 10 minutes, the temperature is brought back to −40° C and the mixture is stirred for 15 minutes. After the addition of saturated ammonium chloride solution and diethyl ether, the organic phase is washed with water, bicarbonate and brine, and then dried. After extraction with ether, the organic phase is washed with brine and dried. After concentration under vacuum, the residue is purified on silica gel (diethyl ether/hexane, 1:9), to give 48 mg of ketone 26a (75% yield).

Spectroscopic data: $^1$H NMR (500 MHz, CDCl$_3$): 7.33 (2H, m), 7.27 (3H, m), 4.87 (1H, k, 5.25 Hz), 3.50 (2H, m), 3.31 (1H, m), 2.62 (1H, dd, 7.33 Hz, 11.7 Hz), 2.51 (1H, dd, 5.0 Hz, 13.4 Hz), 2.45 (1H, td, 0.8 Hz, 13.4 Hz), 2.34 (1H, dd, 4.1 Hz, 13.0 Hz), 1.95 (1H, m), 1.84 (1H, t, 13.0 Hz), 1.78 (1H, m), 1.27 (3H, d, 5.25 Hz), 1.21 (3H, s), 1.19 (3H, s), 1.18 (3H, t, 7.02 Hz), 0.92 (3H, d, 6.44 Hz), 0.78 (3H, s) ppm.

EXAMPLE 28

Conjugate addition to the enone 24: synthesis of 27a (Scheme 3)

A solution of tert-butyllithium (3.342 ml, 1.7 molar in hexane) is added to a solution, cooled to −78° C., of vinyl bromide (0.2 ml) in diethyl ether (1 ml) under an argon atmosphere. After being stirred at −78° C. for three and a half hours, the mixture is added to a suspension of CuCN (127 mg) in diethyl ether (0.5 ml) at −78° C. After 10 minutes, the temperature is brought back to −25° C. and then, after 10 minutes at 0° C., a solution of the enone 24b (70 mg) in ether (1 ml) is added. After 10 minutes, the temperature is brought back to −40° C. and the mixture is maintained for 15 minutes at this temperature. After the addition of ammonia solution, saturated ammonium chloride solution and ether, the organic phase is separated and dried. After concentration under vacuum, the residue is purified on silica gel (diethyl ether/hexane, 1:9), to give 44 mg of ketone 27a (56% yield).

Spectroscopic data for 27a: $^1$H NMR (360 MHz, CDCl$_3$): 5.79 (1H, ddd, 6.8 Hz, 10.3 Hz, 17.1 Hz), 5.02 (1H, dt, 1.3 Hz, 17.1 Hz), 4.97 (1H, dt, 1.2 Hz, 10.3 Hz), 4.86 (1H, h, 5.3 Hz), 3.49 (2H, m), 2.74 (1H, m), 2.44 (1H, dd, 7.4 Hz, 11.7 Hz), 2.34 (1H, dd, 0.9 Hz, 5.2 Hz, 13.7 Hz), 2.19 (1H, dd, 4.1 Hz, 13.2 Hz), 2.10 (1H, ddd, 1.2 Hz, 12.5 Hz, 13.7 Hz), 1.26 (3H, d, 5.3 Hz), 1.20 (3H, s), 1.18 (3H, s), 1.17 (3H, t, 7.0 Hz), 0.96 (3H, d, 6.1 Hz), 0.67 (3H, s) ppm.

MS: m/z: 289 (16), 204 (2.5), 177 (7.3), 149 (12), 137 (6.6), 81 (18), 73 (100).

EXAMPLE 29

Conversion of the olefin 27b to the ketone 30b (Scheme 3)

A solution of 9-borabicyclononane (0.9 ml of a 0.5 molar solution in THF) is added under an argon atmosphere to a solution of 27b (42 mg) in THF (1.5 ml), and the mixture is stirred for 3 hours. Sodium hydroxide (0.35 ml of a 2 N solution in water) is then added, and hydrogen peroxide solution (0.35 ml of 30% solution) is added at 0° C. After being stirred at room temperature for 12 hours, the reaction mixture is poured into water and extracted with ether. The organic phase is washed with bicarbonate and brine and then dried. After concentration under vacuum, the residue is purified on silica gel (ether/hexane, 7:3), to give 26 mg of alcohol 28b (59% yield). This alcohol, dissolved in DMF (0.5 ml) is added to a solution of tert-butyldimethylsilyl chloride (41 mg) and imidazole (54 mg) in DMF (1.7 ml). After the mixture is stirred at room temperature for 4 hours, ice is added and the mixture is extracted with ether and dried. After concentration under vacuum, the residue is purified on silica gel (ether/hexane, 1:9), to give 22 mg of alcohol 29b (68% yield). Oxidation of the latter is performed in dichloromethane (2 ml) in the presence of pyridinium para-toluenesulfonate (18 mg) and pyridinium dichromate (200 mg). After 3 hours, ether is added and the suspension is filtered on celite. The filtrate is washed with saturated copper(II) sulfate solution and dried. After concentration under vacuum, the residue is purified on silica gel (ether/hexane, 1:9), to give 211 mg of ketone 30b (55% yield).

Spectroscopic data: $^1$H NMR (500 MHz, CDCl$_3$): 3.64 (2H, m), 2.44 (1H, ddd, 0.9 Hz, 7.34 Hz, 11.8 Hz), 2.36 (1H, ddd, 1.31 Hz, 5.17 Hz, 13.4 Hz), 2.26 (1H, m), 2.21 (1H, ddd, 1.4 Hz), 4.44 Hz, 13.0 Hz), 1.93 (1H, ddd, 1.43 Hz, 12.0 Hz, 13.5 Hz), 1.20 (6H, s), 0.98 (3H, d, 6.2 Hz), 0.89 (9H, s), 0.65 (3H, s), 0.10 (15H, 3s) ppm.

EXAMPLE 30

Synthesis of the 11β-substituted ketone 38a from 26a (Scheme 3)

A solution of the ketone 26a (60 mg) in THF (0.5 ml) is added at −78° C. to a solution of lithium diisopropylamide, obtained from diisopropylamine (0.024 ml) and n-butyllithium (0.084 ml of a 2 molar solution in hexane) in THF (0.5 ml). The temperature is brought back to −40° C. for 10 minutes. A solution of phenylselenyl bromide (40 mg) in THF (0.5 ml) is then added dropwise at −78° C. Water and ether are added. The organic phase is washed with water, bicarbonate and brine, and dried. After concentration under vacuum, the residue is purified on silica gel (ether/hexane, 1:9), to give 40 mg of selenide 32a (50% yield).

To a solution of the latter in dichloromethane (1 ml) at −15° C., a solution of meta-chloroperbenzoic acid (53 mg) in dichloromethane (1 ml) is added during a period of 10 minutes. Saturated bicarbonate and ether are added. The organic phase is washed with brine and dried. After concentration under vacuum, the residue is purified on silica gel (diethyl ether/hexane, 1:9), to give 5 mg of enone 35a (20% yield).

A solution of this enone (13 mg) in ethyl acetate (2 ml), containing triethylamine (0.12 ml) and 10% palladium/C, is reduced under a hydrogen pressure of 3.4 atmospheres for 20 hours. After filtration on celite, the filtrate is concentrated under vacuum and the residue is purified by chromatography on silica gel (ethyl ether/hexane, 1:9), to give 4 mg of ketone 38a (30% yield) as well as 4 mg of derivative in which the keto group has been reduced.

Spectroscopic data: $^1$H NMR (500 MHz, CDCl$_3$): 7.33 (2H, m), 7.23 (3H, m), 4.87 (1H, k, 5.23 Hz), 3.50 (2H, m), 3.41 (1H, m), 2.94 (1H, dd, 8.10 Hz, 10.9 Hz), 2.58 (1H, dd, 12.7 Hz, 18.6 Hz), 2.54 (1H, dd, 3.6 Hz, 18.6 Hz), 2.39 (1H, dd, 8.0 Hz, 14.1 Hz), 2.00 (1H, m), 1.77 (1H, m), 1.76 (1H, dd, 10.7 Hz, 14.1 Hz), 1.68 (1H, m), 1.27 (3H, d, 5.25 Hz), 1.20 (3H, s), 1.18 (3H, s), 1.17 (3H, t, 6.95 Hz), 0.89 (3H, d, 6.50 Hz), 0.80 (3H, s) ppm.

EXAMPLE 31

Synthesis of the ketone 37a (Scheme 3)

The synthesis may be performed starting from the ketone 25a, according to Example 30. From the enone 24a, the following method also gives the ketone 37a.

A solution of methyllithium (0.74 ml of a 1.4 molar solution in diethyl ether) is added to a suspension of CuI (98 mg) in ether (0.4 ml) at 0° C. After the mixture is stirred for a period of 20 minutes, a solution of the enone 24a (60 mg) in ether (0.5 ml) is added. After being stirred for 30 minutes, the mixture is cooled to −78° C. At this temperature, a solution of phenylselenyl bromine (45 mg) is added dropwise. The mixture is then poured into saturated ammonium chloride solution, which is extracted with ether. After being washed with water, bicarbonate and brine, the organic phase is dried. After concentration under vacuum, the residue is dissolved in dichloromethane (1 ml) at −15° C. and treated with metachloroperbenzoic acid (20 mg) in dichloromethane (1 ml). The reaction mixture is then poured into saturated bicarbonate and extracted with ether. The organic phase is washed with brine and dried. After concentration under vacuum, the residue is purified on silica gel (ether/hexane, 1:9), to give 5 mg of enone 34a (48% yield). The hydrogenation is performed as described above in Example 30. The ketone 37a is obtained in a 62% yield.

Spectroscopic data: $^1$H NMR (500 MHz, CDCl$_3$): 4.87 (1H, k, 5.25 Hz), 3.50 (2H, m), 2.76 (1H, dd, 8.05 Hz, 11.0 Hz), 2.34 (1H, dd, 4.52 Hz, 18.5 Hz), 2.25 (1H, m), 2.15 (1H, dd, 7.78 Hz, 13.8 Hz), 1.98 (1H, dd, 12.2 Hz, 18.6 Hz), 1.94 (1H, m), 1.70 (1H, m), 1.60 (1H, m), 1.27 (3H, d, 5.29 Hz), 1.21 (3H, s), 1.19 (3H, s), 1.18 (3H, t, 7.04 Hz), 1.00 (3H, d, 6.51 Hz), 0.94 (3H, d, 6.49 Hz), 0.69 (3H, s) ppm.

EXAMPLE 32

Synthesis of the 11β-substituted ketone 39a from 14a (Scheme 3)

The procedure is in all respects similar to that described in Example 30.

Spectroscopic data for 39a: $^1$H NMR (360 MHz, CDCl$_3$): 4.87 (1H, k, 5.24 Hz), 4.56 (1H, k, 2.3 Hz, 4.2 Hz), 3.81 (2H, m), 3.48 (4H, m), 2.78 (1H, dd, 8.17 Hz, 10.7 Hz), 2.43 (1H, m), 2.30 (1H, m), 2.18 (1H, m), 2.00 (1H, dd, 12.2 Hz, 18.5 Hz), 1.27 (3H, 2d, 4.95 Hz), 1.20 (3H, s), 1.18 (3H, s), 1.17 (3H, t, 6.88 Hz), 0.93 (3H, d, 6.35 Hz), 0.69 (3H, s) ppm.

EXAMPLE 33

Condensation of 14a with 40; synthesis of 43a (Scheme 4a)

A solution of n-butyllithium (68, 4 μl of a 2.10 molar solution in hexane) was added under argon to a cooled (−78° C.) solution of phosphonate 40 (Ref. 1; 92 mg) in anhydrous tetrahydrofuran (0.75 ml). After the mixture was stirred for 30 minutes at −78° C., a solution of ketone 14a (40 mg) in anhydrous tetrahydrofuran (0.8 ml) was added dropwise, and the resulting solution was stirred at −78° C. for 1 hour and a half. The mixture was brought to room temperature, treated with water (2 drops) and concentrated under vacuum. The residue was purified by chromatography on silica gel (5% ethyl acetate in hexane) to give the desired protected triene 43a.

Spectroscopic data: $^1$H NMR (360 MHz, CDCl$_3$): 6.24 (1H, d: 11.3 Hz), 6.01 (1H, d: 11.3 Hz), 5.18 (1H, s), 4.87 (1H, s), 4.62 (1H, m), 4.37 (1H, m), 4.20 (1H, m), 3.86 (2H, m), 3.49 (2H, m), 1.18 (6H, 2s), 0.91 (3H), 0.88 (17H, s), 0.86 (9H, s), 0.54 (3H, s), 0.08 (18H, br, s) ppm.

EXAMPLE 34

Selective deprotection of 43a; synthesis of 45a and formation of the hemisuccinate 46a (Scheme 4a)

(1) Synthesis of 45a

A solution anhydrous magnesium bromide (6 equivalents) in ether was added to a solution of protected triene 43a in ether. After 2 hours, further magnesium bromide was added. After 4 hours, the reaction mixture was poured into saturated NaHCO$_3$ solution and extracted with ether. The organic phase was washed with brine, dried (Na$_2$SO$_4$) and concentrated under vacuum. After purification of the residue by chromatography on silica gel (eluent: ether/hexane), the silylated triene 45a was obtained in a 61% yield.

(2) Formation of the hemisuccinate 46a

The triene 45a (3 mg) was stirred at room temperature under an argon atmosphere in a solution of succinic anhydride (10 equivalents) in anhydrous pyridine (0.1 ml) in the presence of a catalytic amount of 4-dimethylaminopyridine.

When the reaction was complete (10 days), the pyridine was removed under vacuum and the residue taken up with ether and then filtered. The product was purified by column chromatography on silica gel (Merck Silica gel 60, 230-400 mesh) with hexane/ethyl acetate (7:3), which gave the ester 46a (3.37 mg; 70%).

Spectroscopic data: MS: m/z at 803, 772, 672, 671, 624, 539, 520, 388, 379, 353, 248 and 75.

EXAMPLE 35

Condensation of 30b with 40; synthesis of 44b (Scheme 4a)

The synthesis is performed according to the procedure described for the condensation of 14a with 40 (Example 33). Purification is accomplished by chromatography on an HPLC silica gel 10 μm column, with hexane/ether (99:1). From 63 mg of ketone 30b, 93 mg of triene 44b was obtained (86% yield).

Spectroscopic data: $^1$H NMR (360 MHz, CDCl$_3$): 6.25 (1H, d, 11.2 Hz), 6.02 (1H, d, 11.2 Hz), 5.17 (1H, d, 2.4 Hz), 4.86 (1H, d, 2.4 Hz), 4.37 (1H, dd, 3.7, 6.2 Hz), 4.20 (1H, m), 3.69 (2H, t, 6.5 Hz), 2.88 (1H, dd, 4.0, 13.9 Hz), 2.46 (1H, dd, 3.2, 13.1 Hz), 2.22 (1H, dd, 7.7, 13.1 Hz), 2.03 (1H, dd, 3.6, 12.6 Hz), 1.95 (1H, t, 10.0 Hz), 1.20 (6H, s), 0.94 (3H, d, 6.3 Hz), 0.91 (9H, s), 0.88 (9H, s), 0.87 (9H, s), 0.53 (3H, s), 0.10 (9H, s), 0.06 (18H, 3s). MS: m/z at 876 (9), 875 (13), 874 (9), 743 (78), 248 (100), 1.31 (47), 75 (76) and 73 (58).

EXAMPLE 36

Condensation of 14b with 40; synthesis of 43b (Scheme 4a)

The synthesis is performed according to the procedure described for the condensation of 14a with 40 (Example 33). Purification is accomplished by chromatography on silica gel with hexane/ether (96:4), to give 243 mg of protected triene 43b from 184 mg of ketone 14b (75% yield).

Spectroscopic data: UV (MeOH) $\lambda_{max}$=263 nm; $^1$H NMR (360 MHz, CDCl$_3$): 6.24 (1H, d, 11.2 Hz), 6.02 (1H, d, 11.2 Hz), 5.18 (1H, brs), 4.86 (1H, brs), 4.62 (1H, q, 3.4 Hz), 4.37 (1H, dd, 3.2, 6.0 Hz), 4.19 (1H, m), 3.86 (2H, m), 3.48 (2H, m), 2.90 (1H, m), 2.45 (1H, bd, 13.1 Hz), 2.22 (1H, dd, 7.7, 13.4 Hz), 2.08 (1H, m), 1.96 (1H, t, 9.7 Hz), 1.20 (6H, s), 0.93 (3H, d, 6.2 Hz), 0.87 (18H, s), 0.54 (3H, s), 0.10 (9H, s), 0.06 (12H, s) ppm. MS: m/z at 846 (17), 844 (20), 760 (30), 713 (24), 629 (28), 627 (30), 248 (84), 131 (66), 85 (74), 75 (100), 73 (69), 55 (28), 44 (19).

EXAMPLE 37

Synthesis of the tetrol 49 (Scheme 4a)

(1) By deprotection of 45a

A solution of the triene 45a in anhydrous THF was treated with 10 equivalents of tetrabutylammonium fluoride in THF (1 M solution). The reaction flask was placed under argon, sealed and stirred at 60° C. for several days. After dilution with methylene chloride, the solution was chromatographed and the tetraol 49 was eluted with methylene chloride/methanol (9:1).

(2) By deprotection of 43b

Amberlyst-15 (9g; washed 3 times with methanol) is added to a solution of triene 43b (239 mg) in methanol/THF (1:1; 30 ml; anhydrous and free from oxygen). The flask is placed under argon, protected from light and stirred at room temperature for 6 hours. The resin is filtered off and washed 3 times with methanol. 28% ammonium hydroxide (1 drop) is added to the combined filtrates. After concentration under vacuum, the tetraol is purified by chromatography [silica gel 230-400 mesh, elution with dichloromethane/methanol (9:1); then on HPLC 10 μm column with the same eluent], to give 114 mg of 49 (88% yield).

(3) By deprotection of 44b

Tetrabutylammonium fluoride (1.04 ml of a 1 M solution in anhydrous THF) is added to a solution of protected triene 44b (91 mg) in anhydrous THF (0.83 ml). The flask is placed under argon, protected from light and stirred at room temperature for 70 hours. After concentration under vacuum, the residue is purified as described above (Example 37(2)), to give 45 ml of tetraol 49 (94% yield).

Spectroscopic data for 49: UV (MeOH) $\lambda_{max}$=265 nm; IR: 3340, 2940, 2870, 1645, 1570, 1545, 1380, 1365, 1310, 1215, 1150, 1060, 960, 915, 895, 870, 800, 740 cm$^{-1}$. $^1$H NMR (360 MHz, CDCl$_3$): 6.37 (1H, d, 11.2 Hz), 6.02 (1H, d, 11.2 Hz), 5.33 (1H, br s), 4.99 (1H, br s), 4.43 (1H, m), 4.23 (1H, m), 3.73 (2H, t, 6.7 Hz), 2.89 (1H, dd, 3.9, 13.3 Hz), 2.60 (1H, dd, 3.5, 13.5 Hz), 2.32 (1H, dd, 6.5, 13.4 Hz), 1.21 (6H, s), 0.94 (3H, d, 6.4 Hz), 0.55 (3H, s) ppm. MS: m/z at 460 (6), 442 (62), 424 (11), 406 (16), 217 (21), 152 (23), 134 (78), 105 (25) and 59 (100).

EXAMPLE 38

Synthesis of the hemisuccinate 50 (Scheme 4a)

(I) From the tetratol 49

A solution of the tetraol 49 (114 mg) and 4-dimethylaminopyridine (trace) in anhydrous pyridine (1 ml) is treated with succinic anhydride (64 mg). The flask is placed under argon and protected from light, and the solution is stirred at room temperature for 4 days. The pyridine is driven off under a stream of argon and the residue purified on silica gel (230–400 mesh) with dichloromethane/methanol (85:15), to give 83 mg of hemisuccinate 50 (60% yield).

(2) From the protected hemisuccinate 46a

A solution of the protected hemisuccinate 46a in anhydrous tetrahydrofuran was treated with 10 equivalents of tetrabutylammonium fluoride in tetrahydrofuran (1 M solution). The reaction flask was placed under argon, sealed and stirred at 60° C for several days. After dilution with dichloromethane, the solution was chromatographed on Merck Silica gel 60 with dichloromethane/methanol/acetic acid (95:5:1), to give the hemisuccinate 50 (40%) and tetraol 49 (10%).

Spectroscopic data for 50: UV (MeOH) $\lambda_{max}=263$ nm; IR (KBr): 3300, 2940, 2840, 1710, 1635, 1560, 1405, 1375, 1240, 1210, 1175, 1100, 1020, 960 cm$^{-1}$. $^1$H NMR (360 MHz, CD$_3$OD): 6.33 (1H, d, 11.2 Hz), 6.09 (1H, d, 11.2 Hz), 5.29 (1H, br s), 4.89 (1H, br s), 4.35 (1H, t, 5.7 Hz), 4.17 (2H, t, 6.6 Hz), 4.13 (1H, m), 2.94 (1H, dd, 3.5, 13.0 Hz), 2.54 (6H, m), 2.27 (1H, dd, 6.8, 13.4 Hz), 2.10 (1H, dd, 3.2, 12.7 Hz), 2.00 (1H, dd, 7.1, 11.8 Hz), 1.89 (2H, t, 5.3 Hz), 1.16 (6H, s), 0.98 (3H, d, 6.3 Hz), 0.57 (3H, s )ppm. MS of the corresponding n-butyl ester, m/z at 616, 598, 580, 562, 442, 424, 406, 388, 152 and 134.

EXAMPLE 39

Synthesis of the triol 47 (Scheme 4a)

The synthesis of the triol 47 is accomplished by (1) coupling of the ketone.

Spectroscopic data for 41c: $^1$H NMR (360 MHz, CDCl$_3$): 6.25 (1H, d, 11.2 Hz), 6.01 (1H, d, 11.3 Hz), 5.18 (1H, d, 1.67 Hz), 4.87 (1H, k, 5.20 Hz), 4.87 (1H, s of d), 4.37 (2H, dd, 3.55 Hz, 6.51 Hz), 4.19 (1H, m), 3.50 (2H, m), 2.81 (1H, dd, 3.91 Hz, 13.5 Hz), 2.45 (1H, dd, 3.56 Hz, 13.1 Hz), 2.22 (1H, dd, 7.35 Hz, 13.1 Hz), 1.27 (3H, d, 5.26 Hz), 1.20 (3H, s), 1.19 (3H, s), 1.18 (3H, t, 7.07 Hz), 0.94 (3H, d, 6.39 Hz), 0.93 (3H, d, 6.21 Hz), 0.88 (9H, s), 0.87 (9H, s), 0.53 (3H, s), 0.06 (12H, 2s) ppm.

Spectroscopic data for 47: $^1$H NMR (360 MHz, CD$_3$OD): 6.33 (1H, d, 11.2 Hz), 6.08 (1H, d, 11.2 Hz), 5.39 (1H, dd, 1.19 Hz, 2.16 Hz), 4.89 (1H, d, 1.99 Hz), 4.35 (1H, t, 5.90 Hz), 4.12 (1H, m), 2.85 (1H, dd, 3.98 Hz, 13.4 Hz), 2.52 (1H, dd, 3.46 Hz, 13.3 Hz), 2.26 (1H, dd, 6.72 Hz, 13.4 Hz), 1.16 (6H, s), 0.97 (3H, d, 5.72 Hz), 0.96 (3H, d, 6.15 Hz), 0.57 (3H, s) ppm.

EXAMPLE 40

Synthesis of the triol 48 (Scheme 4a)

The synthesis of the triol 48 is performed in the same manner as for the synthesis of the derivative 47 (Example 39).

Spectroscopic data for 48: $^1$H NMR (360 MHz, CD$_3$OD): 7.27 (4H, m), 7.17 (1H, m), 6.31 (1H, d, 11.0 Hz), 6.16 (1H, d, 11.2 Hz), 5.31 (1H, bs), 4.92 (1H, bs), 4.36 (1H, t, 5.82 Hz), 4.12 (1H, m), 2.98 (1H, dd, 4.40 Hz, 13.1 Hz), 2.86 (1H, m), 2.50 (1H, dd, 3.59 Hz, 13.4 Hz), 2.24 (1H, dd, 6.89 Hz, 13.5 Hz), 2.16 (2H, m), 1.16 (6H, 2s), 0.93 (3H, d, 4.98 Hz), 0.71 (3H, s) ppm.

EXAMPLE 41

Condensation of 14a with 51 (Scheme 4b)

According to a protocol similar to that described for the coupling of 14a and 40, the ketone 14a (32 mg) gave the protected triene 52a (11 mg; 70%).

Spectroscopic data: $^1$H NMR (360 MHz, CDCl$_3$): 7.68 (4H, m), 7.40 (6H, m), 6.03 (1H, d : 11.9 Hz), 5.99 (1H, d : 11.9 Hz), 4.98 (1H, d), 4.75 (1H, d), 4.61 (1H, m), 3.50 (2H, m), 3.39 (3H, m), 2.85 (1H, m), 1.18 (3H, s), 1.17 (3H, s), 1.05 (9H, s), 0.93 (3H, d : 6.2 Hz), 0.85 (9H, s), 0.52 (3H, s), 0.071 (3H, s), 0.056 (3H, s) ppm.

EXAMPLE 42

Selective deprotection of 52a (Scheme 4b)

Under the same reaction conditions as described for 43a, the primary alcohol 54a was obtained (11 mg; 61% yield) from 52a (27 mg).

Spectroscopic data: $^1$H NMR (360 MHz, C$_6$D$_6$): 7.85 (4H, m), 7.25 (6H, m), 6.49 (1H, d : 11.3 Hz), 6.44 (1H, d : 11.3 Hz), 5.12 (2H, s), 4.1 (1H, m), 3.48 (2H, m), 1.22 (15H, s), 1.15 (3H, d), 1.05 (9H, s), 0.65 (3H, s), 0.20 (6H, s) ppm.

EXAMPLE 43

Condensation of 14b with 51 (Scheme 4b)

According to a protocol similar to that described for the coupling of 14a and 51 (Example 41), the ketone 14b (181 mg) gave the protected triene 52b (257 mg; 81%).

Spectroscopic data UV (MeOH) $\lambda_{max}=263$ nm; $^1$H NMR (360 MHz, CDCl$_3$): 7.68 (4H, t, 7.3 Hz), 7.39 (6H, m), 6.02 (1H, d, 11.8 Hz), 5.99 (1H, d, 11.8 Hz), 4.98 (1H, d, 2.5 Hz), 4.75 (1H, d, 2.5 Hz), 4.62 (1H, q, 3.0 Hz), 3.88 (3H, m), 3.48 (2H, m), 2.85 (1H, m), 2.34 (3H, m), 1.20 (6H, s), 1.05 (9H, s), 0.93 (3H, d, 6.2 Hz), 0.52 (3H, s), 0.10 (9H, s) ppm. MS m/z at 839, 755, 754, 753, 317, 239, 199, 131, 85, 75, 73, 69, 57, 55, 45 and 44.

EXAMPLE 44

Condensation of 30b with 51 (Scheme 4b)

According to a protocol similar to that described for the coupling of 14b with 51 (Example 43), the ketone 30b (26 mg) gave the triene 53b (39 mg; 88%).

Rf (hexane/diethyl ether, 99:1) =0.24.

EXAMPLE 45

Synthesis of the triol 56 (Scheme 4b)

(1) From the protected triene 53b

According to a protocol similar to that described for the deprotection of 44b (Example 37(3)), 9 mg of triol 56 (98% yield) is obtained after 17 hours from 18 mg of triene 53b.

(2) From the protected triene 52b

A solution containing the triene 52b (255 mg) and Amberlyst-15 (20 g, washed 3 times with methanol) in methanol/THF, anhydrous and deoxygenated (30 ml, 1:1) is placed under argon, protected from light and stirred at room temperature for 2.5 hours. After filtration and washing of the resin with methanol, the combined filtrates are treated with 28% ammonium hydroxide (1 drop). After concentration under vacuum, the residue is dissolved in anhydrous THF (1 ml) and treated with tetrabutylammonium fluoride (0.9 ml of a 1 M solution in THF). The flask is placed under argon and protected from light and the solution is stirred at room temperature for 45 hours. The THF is driven off under a stream of argon and the residue is purified by chromatography on silica gel followed by HPLC, to obtain 117 g of triol 56 (87% yield).

Spectroscopic data: UV (MeOH) $\lambda_{max}=263$ nm; IR : 3350, 3080, 3040, 2940, 2870, 1680, 1465, 1440, 1380, 1360, 1265, 1215, 1160, 1050, 960, 940, 910, 890, 860, 820 and 740 cm$^{-1}$. $^1$H NMR (360 MHz, CDCl$_3$): 6.22 (1H, d, 11.2 Hz), 6.03 (1H, d, 11.2 Hz), 5.05 (1H, d, 2.3 Hz), 4.81 (1H, d, 2.3 Hz), 3.95 (1H, m), 3.72 (2H, t, 6.7 Hz), 2.88 (1H, dd, 3.9, 13.3 Hz), 2.58 (2H, dd, 3.4, 13.2 Hz), 2.40 (1H, ddd, 4.9, 7.7, 12.9 Hz), 2.29 (1H, dd, 7.4, 13.0 Hz), 2.17 (1H, ddd, 5.1, 8.5, 13.2 Hz), 1.21 (6H, s), 0.94 (3H, d, 6.4 Hz), 0.55 (3H, s) ppm. MS m/z at 445, 426, 411, 136, 118, 105, 91, 81, 69, 59, 55, 43.

EXAMPLE 46

Synthesis of the hemisuccinate 57 (Scheme 4b)

A solution of triol 56 (91 mg) and 4-dimethylaminopyridine (trace) in anhydrous pyridine (1 ml) is treated with succinic anhydride (31 mg). The flask is placed under argon and protected from light and the solution is stirred at room temperature for 45 hours. The pyridine is driven off under argon and the residue is purified by chromatography on silica gel (230–400 mesh) with dichloromethane/methanol (9:1), and then by reversed-phase HPLC on a C$_{18}$-silica gel 10 μm column eluted with methanol/water (3:1), to give 65 mg of 57 (58% yield).

Spectroscopic data UV (MeOH) $\lambda_{max}=263$ nm; $^1$H NMR (360 MHz, CDCl$_3$): 6.23 (1H, d, 11.2 Hz), 6.04 (1H, d, 11.2 Hz), 5.04 (1H, d, 2.3 Hz), 4.81 (1H, d, 2.3 Hz), 4.20 (2H, t, 6.4 Hz), 3.98 (1H, m), 2.91 (1H, dd, 3.9, 13.4 Hz), 2.65 (4H, m), 2.59 (1H, m), 2.40 (1H, m), 2.31 (1H, dd, 7.4, 12.9 Hz), 2.18 (1H, ddd, 5.1, 8.6, 13.3 Hz), 2.03 (1H, dd, 3.1, 12.4 Hz), 1.21 (6H, s), 0.94 (3H, d, 6.4 Hz), 0.54 (3H, s) ppm. MS m/z at 545, 527, 508, 444, 426, 408, 136, 118, 81, 69, 59, 55 and 44.

EXAMPLE 47

Synthesis of the triol 63 (Scheme 4c)

(1) Coupling of the ketone 37c with 40 to give 59c

The synthesis is performed according to the same procedure as for the synthesis of 41c, starting with 25c, and gives the protected triene 59c (6 mg; 27% yield) from 14 mg of ketone 37c.

(2) The hydrolysis of 59c is performed with Amberlyst resin according to the procedure described for the conversion of 43b and 49 (Example 37(2)).

EXAMPLE 48

Synthesis of the tetraol 65 (Scheme 4c)

(1) Coupling of the ketone 39c with 40 to give 61c

The synthesis is performed in the same manner as described for 59c. 3 mg of protected triene 61c are obtained from 10 mg of ketone (20% yield).

Spectroscopic data: $^1$H NMR (360 MHz, CDCl$_3$) 6.14 (1H, d, 11.3 Hz), 6.05 (1H, d, 11.3 Hz), 5.18 (1H, br s), 4.88 (1H, q, 5.7 Hz), 4.87 (1H, br s), 4.59 (1H, m), 4.37 (1H, dd, 3.6, 6.4 Hz), 4.19 (1H, m), 3.87 (1H, m), 3.79 (1H, m), 3.48 (4H, m), 2.43 (3H, m), 2.17 (2H, m), 1.27 (3H, d, 5.2 Hz), 1.21 (5H, s), 1.19 (3H, s), 1.18 (3H, t, 7.0 Hz), 0.91 (3H, d, 6.2 Hz), 0.88 (9H, s), 0.87 (9H, s), 0.58 (3H, s), 0.06 (12H, 3s) ppm.

(2) The hydrolysis of 61c is performed with Amberlyst resin according to the procedure described for the conversion of 43b and 49 (Example 37(2)).

Spectroscopic data for 65: UV (MeOH): $\lambda_{max}=265$ nm = 265 nm; $^1$H NMR (360 MHz, CD$_3$OD): 6.24 (1H, d, 11.3 Hz), 6.12 (1H, d, 11.3 Hz), 5.29 (1H, bbs), 4.35 (1H, t, 5.7 Hz), 4.12 (1H, m), 3.59 (2H, m), 2.52 (1H, dd, 3.4, 13.4 Hz), 2.47 (1H, m), 2.44 (1H, m), 2.26 (1H, dd, 6.6, 13.3 Hz), 1.89 (2H, t, 5.6 Hz), 1.16 (6H, s), 0.96 (3H, d, 5.2 Hz) and 0.62 (3H, s) ppm; MS m/z: 460 (M$^+$, 1.4), 442 (23), 424 (5.4), 406 (3.4), 368 (3.0), 313 (2.9), 256 (2.6), 239 (3.0), 185 (3.0), 157 (3.7), 105 (9.6).

EXAMPLE 49

Synthesis of the enone 66 (R'=TBDPS) from the diol 20 (R'=H) (Scheme 5)

A solution of tert-butyldiphenylsilane (0.785 g) and imidazole (0.56 g) in DMF (15 ml) is added dropwise to a solution of the diol 20 (R'=H) (0.138 g) in anhydrous DMF (5 ml). After the mixture is stirred at room temperature for 2 hours, ice and brine are added, followed by an extraction with ether. The extract is dried and concentrated under vacuum and the residue is purified over silica gel (ether/hexane, 1:9), to give 0.19 g of the alcohol 20 (R'=TBDPS) (65% yield).

Spectroscopic data for 20 (R'=TBDPS): $^1$H NMR (360 MHz, CDCl$_3$): 7.67 (4H, m), 7.40 (6H, m), 4.07 (1H, br s), 3.62 (1H, dd, 3.3, 9.7 Hz), 3.37 (1H, dd, 6.9, 9.7 Hz), 2.01 (1H, m), 1.08 (3H, d, 6.6 Hz), 1.06 (9H, s), 0.91 (3H, s) ppm. MS: m/z: 393 (58), 375 (29), 315 (9), 297 (9), 239 (9), 199 (100), 183 (22), 177 (53), 151 (21), 135 (54), 121 (22), 95 (67), 55 (29).

A solution of the alcohol 20 (R'=TBDPS) (0.19 g) in dichloromethane (5 ml) containing pyridine paratoluenesulfonate (0.02 g) and pyridine dichromate (0.25 g) is stirred at room temperature for 1 hour. The reaction mixture is then diluted with ether and filtered on celite. The filtrate is washed with saturated copper sulfate, dried and concentrated under vacuum. Purification of the residue on silica gel (5% to 10% diethyl ether/hexane) gives 0.15 g of the corresponding ketone (80% yield).

Spectroscopic data: $^1$H NMR (360 MHz, CDCl$_3$): 7.66 (4H, m), 7.40 (6H, m), 3.61 (1H, dd, 2.7, 9.8 Hz), 3.41 (1H, dd, 6.1, 9.8 Hz), 2.42 (1H, dd, 7.6, 11.3 Hz), 2.25 (2H, m), 2.12 (1H, m), 2.01 (1H, m), 1.12 (3H, d, 6.2 Hz), 1.06 (9H, s), 0.61 (3H, s), MS: m/z: 448 (M$^+$), 391 (100), 313 (3), 295 (4), 283 (2), 239 (7), 199 (74), 175 (27), 135 (27).

A solution of the ketone (0.14 g) in THF (1 ml) is added dropwise over a period of 10 minutes to a solution, cooled to −78° C., containing lithium diisopropylamide, prepared from diisopropylamine (0.053 ml) and n-butyllithium (0.152 ml of a 2.45 M solution in hexane) at −20° C., in THF (1 ml). After the mixture is stirred at −40° C., a solution of phenylselenyl bromide (0.088 g) in THF (0.5 ml) is added. After the addition of saturated ammonium chloride solution and ether, the organic phase is washed with water, saturated bicarbonate and brine, and dried. After concentration under vacuum, the residue is purified on silica gel (3% to 15% diethyl ether/hexane), to give 0.142 g of the selenide (75% yield).

A solution of meta-chloroperbenzoic acid (0.067 g) in dichloromethane (2 ml) is added dropwise over a period of 10 minutes to a solution, cooled to 15° C., of the selenide (0.14 g) in dichloromethane (2 ml). The reaction mixture is then poured into saturated bicarbonate solution, which is extracted with ether. The organic phase is washed with brine and dried. After concentration under vacuum, the residue is purified on silica gel (3% to 20% diethyl ether/hexane), to give 0.08 g of enone 66 (R'=TBDPS) (77% yield).

Spectroscopic data for 66 (R'=TBDPS): $^1$H NMR (360 MHz, CDCl$_3$): 7.66 (4H, m), 7.41 (6H, m), 6.77 (1H, ddd, 2.2, 5.7, 9.9 Hz), 5.99 (1H, ddd, 0.8, 3.1, 9.9 Hz), 3.62 (1H, dd, 3.1, 9.8 Hz), 3.42 (1H, dd, 6.3, 9.8 Hz), 2.63 (1H, ddd, 0.7, 5.8, 18.5 Hz), 2.55 (1H, t, 9.4 Hz), 2.42 (1H, dt, 2.4, 18. (Hz), 1.11 (3H, d, 6.4 Hz), 1.07 (9H, s), 0.72 (3H, s). MS: m/z: 446 (M$^+$), 389 (100), 311 (5), 295 (3), 199 (62), 173 (12), 147 (7), 121 (10).

EXAMPLE 50

Synthesis of the derivative 58 from the derivative 57

(1) Activation of the derivative of formula 57 with N-hydroxysuccinimide

A mixture of product of formula 57 ($1.38 \times 10^{-7}$ mol), N-hydroxysuccinimide ($1.5 \times 10^{-7}$ mol) and dicyclohexylcarbodiimide ($1.5 \times 10^{-7}$ mol) in anhydrous dimethylformamide (DMF, 100 μl) is placed in the dark for 16 hours at 25° C.

(2) Radioiodination of tyramine

The reaction is performed in 0.1 M sodium borate buffer at a pH 8. 4 millicuries of Na$^{125}$I (approximately $1.8 \times 10^{-9}$ mol, 40 μl) and then $20 \times 10^{-6}$ g of chloramine T (10 μl) are added to $40 \times 10^{-9}$ mol of tyramine (20 μl). Exactly 60 seconds later, $60 \times 10^{-6}$ g of sodium metabisulfite (30 μl) is added to the reaction mixture.

(3) Coupling of radioiodinated tyramine $34 \times 10^{-9}$ mol of product of formula 57, activated beforehand with N-hydroxysuccinimide (DMF, 25 μl), are treated with $8 \times 10^{-9}$ mol (phosphate buffer, 20 μl). The coupling is performed for 20 hours at 25° C. in the dark. The coupling product, 11α-[2-($^{125}$I-tyramidosuccinovloxy)ethyl]-25-hydroxy-vitamin D$_3$(58) is purified by HPLC (C$_{18}$ column, elution gradient acetonitrile/water from 0 to 100%).

EXAMPLE 51

Preparation of an immunogen: coupling of the derivative of formula 50 to bovine serum albumin (1) Activation of the derivative of formula 50 with N-hydroxysuccinimide A mixture of derivative of formula 50 ($1.3 \times 10^{-6}$ mol), N-hydroxysuccinimide ($1.47 \times 10^{-6}$ mol) and dicyclohexylcarbodiimide ($1.47 \times 10^{-6}$ mol) in anhydrous dimethylformamide (DMF, 100 μl) is stirred for 16 hours at 4° C. in the dark.

(2) Coupling of the activated product to bovine serum albumin

Bovine serum albumin (BSA, $22.5 \times 10^{-9}$ mol) in 0.1 M buffer phosphate pH 7.5 (1.5 ml) is added to 100 μl of activated product ($1.3 \times 10^{-6}$ mol, DMF). The reaction mixture is stirred for 24 hours at 4° C. in the dark, and then dialyzed against sodium chloride solution (9 g/l) at 4° C. The conjugate is used without further treatment as an immunogen.

EXAMPLE 52

Assay method for serum 25-hydroxyvitamin D$_3$ (1) Reagents

Tracer: derivative of formula 58 obtained as described in the present invention (Example 50). Dissolved in ethanol (approximately $5 \times 10^{-5}$ cpm/ml).

Ligand: plasma transporter of vitamin D (DBP prepared from the serum of rats deficient in vitamin D (Ref. 20)). For the purposes of this experiment, the serum was diluted 9000-fold in veronal buffer (composition, see below).

Charcoal/dextran suspension: 2 mg of Norit A (120 mesh) and 0.2 mg of dextran T70 per ml.

Extraction solvent: cyclohexane/ethyl acetate (1:1 vol/vol).

Buffer: 0.1 M veronal pH 8.6, 0.2 g/l sodium merthiolate, 0.1 g/l ovalbumin.

(2) Equipment

Screw-capped glass extraction tubes (10 ml).
Siliconed glass test tubes.
Gamma scintillation counter.
Refrigerated centrifuge (4° C., 1500 g).
Reduced pressure evaporation system.

(3) Assay procedure

A calibration curve is obtained with serum samples precalibrated for the 25-hydroxyvitamin D$_3$ concentration (2.5 to 80 ng/ml).

100 μl of serum treated with 200 μl of water and with 1 ml of extraction solvent are placed in an extraction tube and agitated vigorously for 30 minutes at 20°-25° C.

a 100 μl volume of the organic phase is transferred to a siliconed glass test tube and evaporated under reduced pressure at 40° C.

to the tube containing the extraction residue of 25-hydroxyvitamin D$_3$, 50 μl of the tracer solution ($\approx$25,000 cpm) and 0.5 ml of ligand are added successively. The mixture is agitated and incubated for 1 hour at 4° C.

1 ml of charcoal/dextran suspension is added at 4° C., and the mixture is agitated and incubated for 30 minutes at 4° C.

the mixture is centrifuged (4° C., 1300×g, 10 min), and the radioactivity of 1 ml of supernatant is measured in a gamma scintillation counter.

The calibration curve is plotted using the precalibrated samples of known concentration (cpm=f[concentration]). The concentrations of 25-hydroxyvitamin D$_3$ in the other sera are estimated graphically on the calibration curve.

EXAMPLE 53

Results of an assay using a new $C_{11}$-derivative of vitamin D as an iodinated tracer It has been shown, according to the present invention, that it would be possible to obtain $C^{11}$-derivatives of vitamin D which display an affinity for DBP comparable to the natural metabolite 25-OH-vitamin $D_3$. Existing assays for 25-OH-vitamin $D_3$ in serum are based on competition for DBP (of fish, birds or mammals) on the part of the natural metabolite 25-OH-vitamin $D_3$ and a tritiated tracer [$^3$H]-25-OH-$D_3$, no iodinated tracer being described. The present invention enables, in particular, an iodinated analog of 25-OH-vitamin $D_2$ or 25-OH-vitamin $D_3$ to be used as a tracer. By way of example, the molecule 11$\alpha$-[2-(m-$^{125}$I-tyramidosuccinoyloxy)ethyl]-25-hydroxy vitamin $D_3$ (58) has been used as a tracer and the results of the assay obtained have been compared with those of a conventional assay using [$^3$H]-25-OH-$D_3$. It is found that, for a wide range of values (0–260 ng/ml) reflecting normal and pathological extreme values, correlation between the two assays is exceptional (>0.97; n=204), demonstrating the quality of the assay using an iodinated tracer of the present invention. In particular, this correlation is exceptional for low and paraphysiological values, where the accuracy of the assay is particularly important (correlation coef.>0.97; n=154). In addition, these results show a lower "background" with the iodinated tracer, which constitutes a further advantage compared with the best reference technique available.

EXAMPLE 54

Therapeutic application of the $C^{11}$-derivatives of vitamin $D_3$ (1) Some $C^{11}$-derivatives bind DBP with a high affinity.

The branch at $C^{11}$ does not inhibit the binding of the 25-OH-vitamin $D_3$ analog to DBP. By way of example, FIG. (1) shows that the binding of the derivative 11-(2-hydroxyethyl)-25-OH-vitamin $D_3$ (56) to purified human DBP is similar to that of 25-OH-vitamin $D_3$, and is hence of high affinity. In addition, the addition of a hemisuccinate group, 11-(2-HS-ethyl)-25-OH-vitamin $D_3$ (57) does not necessarily modify this affinity substantially. It is known that 1,25-(OH)$_2$-vitamin $D_3$ has a lower affinity for DBP. This affinity is not modified with an 11-hydroxyethyl derivative. The experiment is comparable with DBP of other origins (fish, birds, mammals), and in particular with rat DBP. In conclusion, the branch at $C^{11}$ does not adversely affect the binding to DBP, and it is possible to conceive of different derivatives having a greater or lesser affinity for DBP. This property has been turned to good account for obtaining analogs which can be iodinated via their branch at $C^{11}$, and these derivatives have been used successfully, for example, for developing the first specific assay for 25-OH-vitamin $D_3$ using an iodinated tracer.

(2) $C^{11}$-derivatives bind the vitamin $D_3$ receptor with a high affinity

The binding of 1,25-(OH)$_2$-vitamin $D_3$ to its intracellular receptor appears to be essential for most of its biological properties.

FIG. (2) shows that the 11$\alpha$-(hydroxyethyl) and 11$\beta$-(2-hemisuccinoyloxyethyl) derivatives of 1,25-(OH)$_2$-vitamin $D_3$ bind the vitamin $D_3$ receptor. The affinity, however, is approximately 100- to 200-fold lower than that of 1,25-(OH)$_2$-vitamin $D_3$. This experiment is reproducible with receptors of different origins (rat duodenum in the example illustrated, but also calf thymus, human lymphocytes, and the like). It is possible to obtain derivatives which have a better affinity for the receptor: for example, the 11$\alpha$-phenyl derivative of 1,25-(OH)$_2$-vitamin $D_3$ binds the receptor better than the 11$\alpha$-hydroxyethyl derivatives, and the 11$\alpha$-methyl derivative binds the receptor with an affinity comparable to unsubstituted 1,25-(OH)$_2$-vitamin $D_3$.

In conclusion, the branch at the $C^{11}$-position enables vitamin $D_3$ analogs to be obtained displaying variable affinities for the specific receptor. Some derivatives have a high affinity, comparable to 1,25-(OH)$_2$-vitamin $D_3$, others have moderate or low affinities. This demonstrates the pharmacological importance of this position for deriving vitamin $D_3$ analogs. (From the diagnostic standpoint, this implies, in particular, the possibility of an assay using the specific receptor, or part of this receptor, and of an iodinated tracer involving the branch at $C^{11}$.)

(3) $C^{11}$-derivatives are biologically active analogs of vitamin $D_3$.

Binding to the receptor suggests the possibility of a biological activity of some $C^{11}$-derivatives of vitamin $D_3$. This is, in effect, directly confirmed in various biological tests (induction of the differentiation HL 60 leukemic cells, inhibition of lymphocyte proliferation, modification of the proliferation of cancer cells, calciotropic effect, and the like). FIGS. (3–4) illustrate the effect of different analogs on the differentiation of HL 60 leukemic cells. It is seen that the derivatives 11-(hydroxyethyl-1,25-(OH)$_2$-vitamin $D_3$ and 11-(hydroxyethyl)-25-OH-vitamin $D_3$ are of low activity, like 25-OH-vitamin $D_3$ (FIG. 3). In contrast, the derivative 11$\alpha$-phenyl-1,25-(OH)$_2$-vitamin $D_3$ is active, and the derivative 11$\alpha$-methyl-1,25-(OH)$_2$-vitamin $D_3$ displays a strong activity, approaching that of 1,25-(OH)$_2$-vitamin $D_3$ (FIG. 4).

In conclusion, the branch at $C^{11}$ enables biologically active analogs of vitamin $D_3$ to be obtained, and the intensity of the biological effect can be modulated in accordance with the substitution at $C^{11}$.

(4) $C^{11}$-derivatives enable a dissociation to be observed between different properties of vitamin $D_3$.

Figure 2:
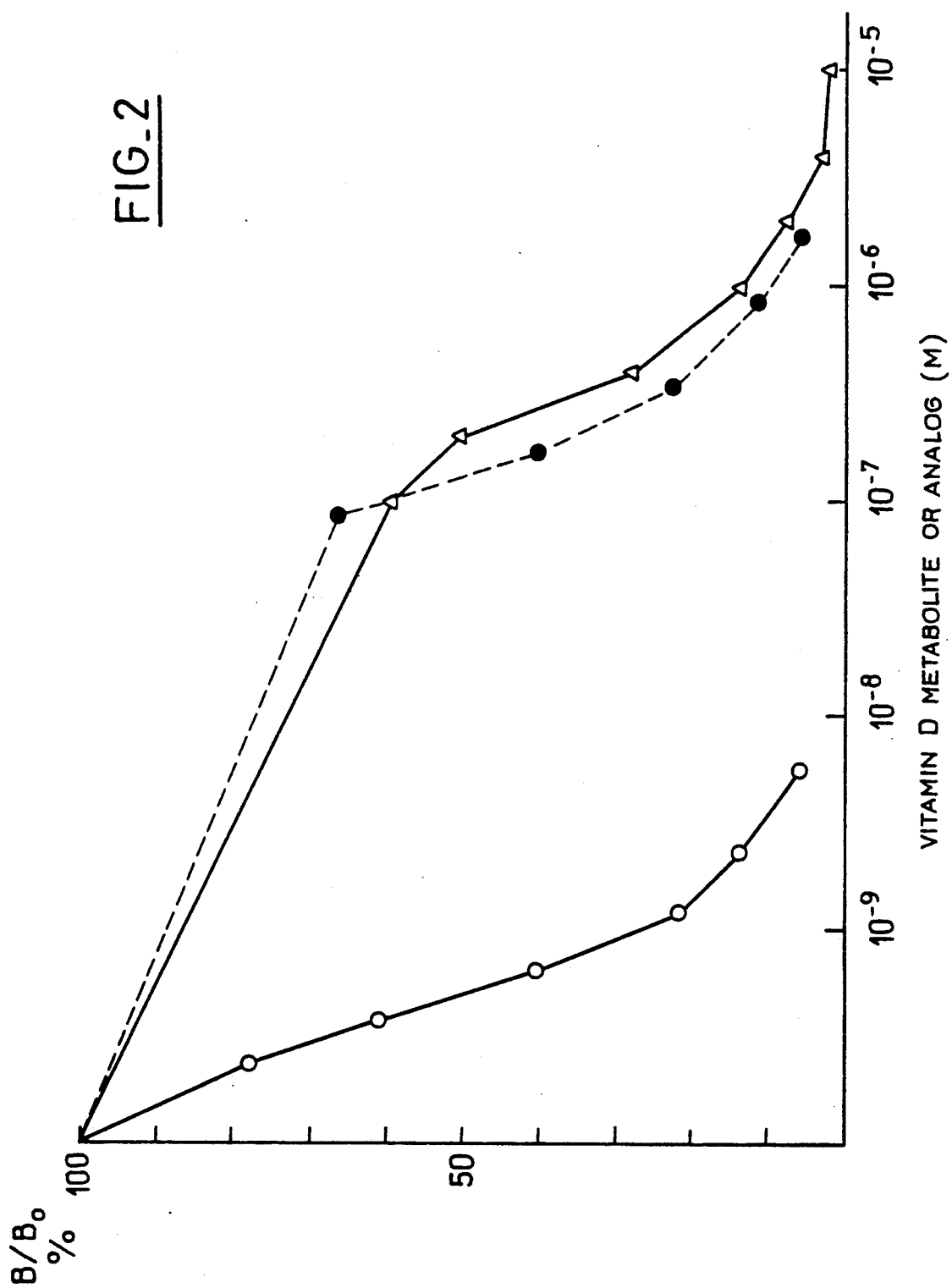

The synthesis of different derivatives enables analogs to be sought which display only partially the different properties of vitamin $D_3$, or in differing proportions. We showed above, by way of example, that binding of the derivatives 11$\alpha$-(hydroxyethyl)-1,25-(OH)$_2$-vitamin $D_3$ and 11$\alpha$-(2-hemisuccinoyloxyethyl vitamin $D_3$ to the vitamin $D_3$ receptor was comparable (FIG. 2). The affinity for the receptor is approximately 100- to 200-fold lower than that of 1,25-(OH)$_2$-vitamin $D_3$. In a biological test (inhibition of lymphocyte proliferation), the 11$\alpha$-(hydroxyethyl) derivative is also 100-fold less active than 1,25-(OH)$_2$-vitamin $D_3$. For the same test, the 11$\alpha$-(2-hemisuccinoyloxyethyl) derivative is approximately 1000-fold less active.

In conclusion, different $C^{11}$-derivatives can display dissociation between their properties, for example differing biological activities and a similar affinity for the receptor.

(5) $C^{11}$-derivatives have a partial antagonist effect with respect to the properties of vitamin $D_3$.

Not only do some $C^{11}$-derivatives bind the receptor and exert agonist activities comparable to 1,25-(OH)$_2$- vitamin $D_3$, but they are also capable of having an antagonist effect. Thus, in a lymphocyte proliferation test, the addition of 1,25-$(OH)_2$-vitamin $D_3$ causes a marked inhibition of proliferation. For example, if the proliferative response of human lymphocytes stimulated with PHA is 100 in the absence of vitamin $D_3$, it is reduced to 66.5 in the presence of $10^{-11}$ M 1,25-$(OH)_2$-vitamin $D_3$ (Table 1). In the same test, the addition of 11-(2-hydroxyethyl)-1,25-$(OH)_2$-$D_3$ induces no inhibition at $10^{-10}$ M (102.6). However, this concentration ($10^{-10}$ M) of the derivative 11-(2-hydroxyethyl)-1,25-$(OH)_2$-$D_3$, added to the inhibitory concentration ($10^{-11}$ M) of 1,25-$(OH)_2$-vitamin $D_3$, antagonizes its inhibitory effect: the proliferation is reduced from 66.5% to 91.8% (Table 1).

TABLE 1

Effect of 1,25-$(OH)_2$-vitamin $D_3$, the 11-(OH-ethyl) derivative and a mixture of the two products on lymphocyte proliferation: the derivative behaves as a partial antagonist of vitamin $D_3$.

| 1,25-$(OH)_2$-vitamin $D_3$ | 11-(2-OH-Ethyl)-1,25-$(OH)_2$-vitamin $D_3$ | |
|---|---|---|
| | 0 | $10^{-10}$M |
| 0 | 100% | 102.6% |
| $10^{-12}$M | 93.8% | 98.5% |
| $10^{-11}$M | 66.5% | 91.8% |

In conclusion, various $C^{11}$-derivatives of $D_3$ display an antagonistic effect on the biologically active form of vitamin $D_3$.

Bibliographic References 21, 22 and 23 served as references for the methodology of the tests of binding to DBP and to the receptor, and of the test of inhibition of lymphocyte proliferation.

References 1. (General bibliography or other patents)
2. V. K. Ostrem and H. F. DeLuca, Steroids (1987) 49, 73; M. S. Calverley, Tetrahedron (1987) 43, 80.
3. E. G. Baggiolini, J. A. Jacobelli, B. M. Hennessy and Uskokovic, J. Am. Chem. Soc., (1982) 104, 2945.
4. (a) H. T. Tok and W. H. Okamura, J. Org. Chem. (1983) 48, 1414; (b) J. L. Mascarenas, A. Mourino and L. Castedo, J. Org. Chem. (1986) 51, 1269.
5. B. J. Magerlin and J. H. Hogg, Tetrahedron (1958) 2 80.
6. M. M. Midland and Y. C. Kwon, Tetrahedron Lett. (1985) 26, 5017.
7. J. Kriz, M. J. Benet and J. Peska, Tetrahedron Lett. (1965) 2881.
8. H. Klein and A. Steinmetz, Tetrahedron Lett. (1975) 4249.
9. G. Hilgers and N. D. Scharf, Tetrahedron Lett. (1984) 1765.
10. F. J. Sardina, A. Mourino and L. Castedo, J. Org. Chem. (1986) 51, 1264.
11. (a) B. M. Trost, T. N. Salzmann and K. Hiroi, J. Am. Chem. Soc. (1976) 98, 4887; (b) H. J. Reich, I. L. Reich and J. M. Renga, J. Am. Chem. Soc. (1973) 95, 5813.
12. H. J. Reich, J. M. Renga and I. L. Reich, J. Org. Chem. (1976) 39, 2133.
13. R. A. Gibbs and W. H. Okamura, Tetrahedron Lett. (1987) 28, 6021.
14. (a) G. H. Posner, Org. React. (1972) 19, 1; (b) B. H. Lipshutz, R. S. Wilhelm and J. A. Kozlowski, Tetrahedron (1984) 40, 5005; B. H. Lipshutz, Synthesis (1987) 325.
15. (a) W. Nagata, M. Yoshioka and S. Hirai, J. Am. Chem. Soc. (1972) 94, 4635; (b) M. Samson and M. Vandewalle, Synthetic communications (1978) 8, 231.
16. E. Hatzigrigoriou, M. C. Roux-Schmitt, L. Wartski and J. Seyden-Penne, Tetrahedron (1988) 44, 4457.
17. B. H. Lipshutz, R. S. Wilhelm, J. A. Kozlowski, J. Org. Chem. (1984) 49, 3938.
18. L. Castedo, A. Mourino and L. A. Sanandeses, Tetrahedron Lett. (1986) 27, 1523 and L. Castedo, J. L. Mascarenas, A. Mourino and L. A. Sanandeses, Tetrahedron Lett. (1988) 29, 1203.
19. L. Castedo, J. L. Mascarenas and A. Mourino, Tetrahedron Lett. (1987) 28, 2099.
20. R. Bouillon, E. Van Herck, I. Jans, B. Keng Tan, H. Van Baelen and P. de Moor, Clin. Chem., 30, 1731, 1984.
21. J. Steroid Biochem Vol. 29, No. 4, pp. 381-386, 1988.
22. Archives of Biochemistry and Biophysics Vol. 217, No. 1, August, pp. 257-263, 1982.
23. The Journal of Biological Chemistry Vol. 253, No. 12 Issue of June, pp. 4426-4431, 1978.

We claim:
1. Vitamin D derivatives corresponding to the following formula I.

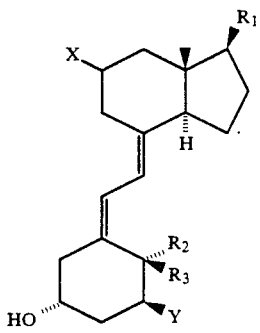

in which
$R_1$ denotes a substituted alkyl group having 1 to 15 carbon atoms wherein the substituent is
  an hydroxyl, ester or ether at one or more positions;
  a methyl or ethyl group at one or more positions;
  a halogen or a plurality of halogens at one or more positions;
  one or more carbon atoms added;
  a substituent formed by replacing one or more carbon atoms of said alkyl group by oxygen, nitrogen or sulfur atoms;
  a ring formed by directly linking carbons $C^{26}$ and $C^{27}$ or by linking said carbons via a chain of 1 to 3 carbon atoms; it being possible for each carbon atom in said chain of carbon atoms to optionally bear any of the groups or modifications described above, and/or
  a saturated, unsaturated, aromatic or heteroaromatic ring, capable of optionally bearing any of the groups and modifications described above, and wherein said alkyl group is
  saturated or unsaturated, and
Y denotes H, OH, ester or ether; and
X denotes
  an alkyl or substituted alkyl chain, saturated or unsaturated, optionally substituted by one or more functional group Z, wherein Z is halogen, hydroxyl, formyl, carboxyl, amine, thiol, cyano, nitro, sulfoxide, sulfone, phosphono, ether, ester, acetal, amide, hydrazine, phosphate or bis(phosphate), or an aromatic or heteroaromatic ring, optionally substituted with halogen, hydroxyl, amine, formyl, carboxyl, thiol, cyano, nitro, ether, ester, ester, acetal or amide, or halogen, cyano, sulfoxide, sulfone, hydroxyl, thiol, amine, ether, ester, or hydrazine; and $R_2$ denotes a methyl group and $R_3$ an H, or $R_2$ is H and $R_3$ is methyl, or $R_2$ and $R_3$ are H, or alternatively $R_2$ and $R_3$ together denote a methylene group $=CH_2$.

2. The derivatives as claimed in claim 1, in which $R_1$ denotes one of the following chains

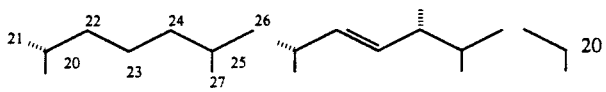

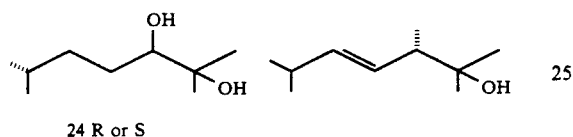

24 R or S

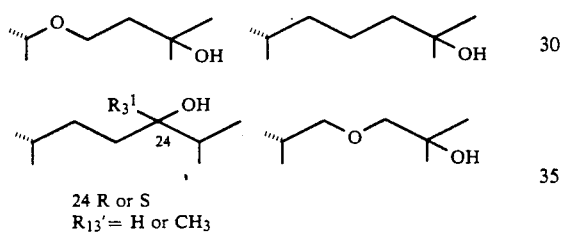

24 R or S
$R_{13}' = H$ or $CH_3$

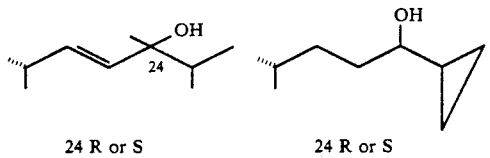

24 R or S     24 R or S

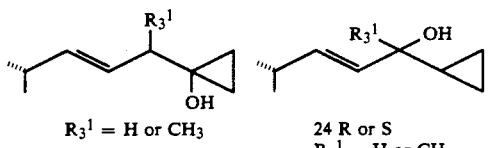

$R_3^1 = H$ or $CH_3$     24 R or S
$R_3^1 = H$ or $CH_3$

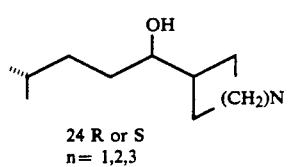

24 R or S
n = 1,2,3

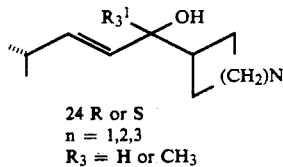

24 R or S
n = 1,2,3
$R_3 = H$ or $CH_3$

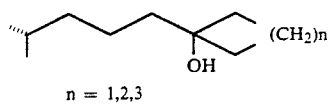

n = 1,2,3

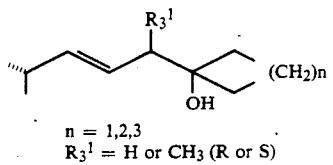

n = 1,2,3
$R_3^1 = H$ or $CH_3$ (R or S)

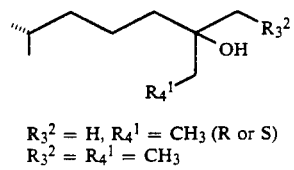

$R_3^2 = H$, $R_4^1 = CH_3$ (R or S)
$R_3^2 = R_4^1 = CH_3$

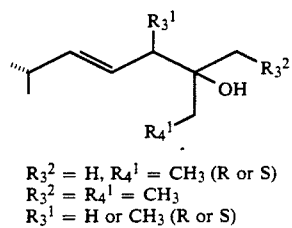

$R_3^2 = H$, $R_4^1 = CH_3$ (R or S)
$R_3^2 = R_4^1 = CH_3$
$R_3^1 = H$ or $CH_3$ (R or S)

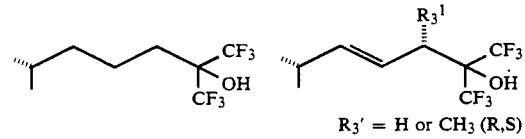

$R_3' = H$ or $CH_3$ (R,S)

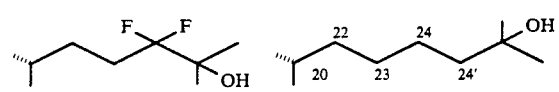

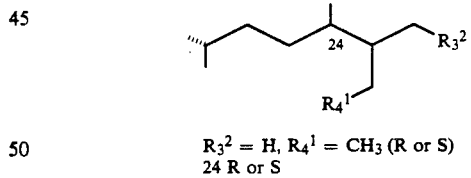

$R_3^2 = H$, $R_4^1 = CH_3$ (R or S)
24 R or S

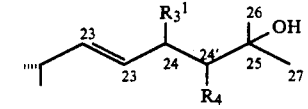

$R_3^1 = R_4^2 = H$
$R_3^1 = CH_3$ (R or S), $R_4^2 = H$
$R_3^1 = H$ $R_4^2 = CH_3$ (R or S)

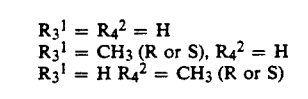

3. Vitamin $D_3$ derivatives corresponding to the formula I'

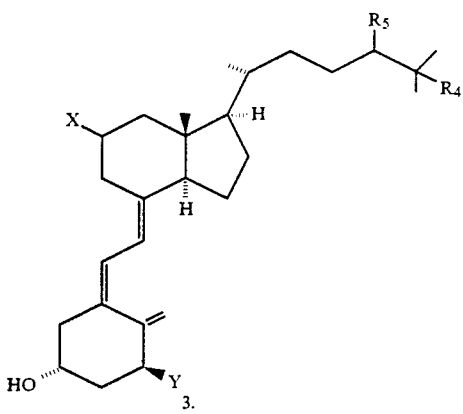

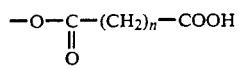

which
- Y, $R_4$ and $R_5$ denote H or OH, and
- X denotes an alkyl chain of 1 to 6 carbon atoms, optionally substituted, with a functional group Z, wherein Z is an hydroxyl, formyl, carboxyl, amine, amide ester, ether or acetal group, X being in the α or β isomeric form.

4. The derivatives as claimed in claim 3, in which (Y, $R_4$, $R_5$) is chosen from (H, OH, H), (OH, OH, H), (H, H, OH), (H, OH, OH), (OH, H, OH), (OH, H, H).

5. A Vitamin $D_3$ derivative according to claim 3, wherein Z is at the terminus of X.

6. The derivatives as claimed in claim 5, in which X denotes (2-Z-ethyl), a methyl or a phenyl.

7. The derivatives as claimed in claim 5, in which Z denotes a $$-O-\underset{\underset{O}{\|}}{C}-(CH_2)_n-COOH$$

group with n between 2 and 10, or an OH group.

8. A vitamin D derivative according to claim 1, wherein $R_2$ denotes the side chains of vitamin $D_2$ ($C^{20}$ to $C^{28}$) or $D_3$ ($C^{20}$ to $C^{27}$);
- said hydroxyl, ester or ether is at positions 24-, 25- and/or 26-;
- said methylation or ethylation is at positions 24-, 26- and/or 27-;
- said halogenated or polyhalogenated is perfluoro at the 26- and/or 27-positions or difluoro at the 24-position;
- said added carbon atom(s) is between positions 24- and 25-;
- said substitution of one or more carbon atoms by an oxygen, sulfur or nitrogen atom is at positions 22-, 23- or 24-; or
- said ring formation is a bond between $C^{26}$ and $C^{27}$ or a chain of from 1 to 3 carbon atoms.

* * * * *

UNITED STATES PATENT AND TRADEMARK OFFICE
CERTIFICATE OF CORRECTION

PATENT NO. : 5,093,519

DATED : March 3, 1992

INVENTOR(S) : Bouillon et al.

It is certified that error appears in the above-identified patent and that said Letters Patent is hereby corrected as shown below:

On the title page: Column 1, line 1
  At [54], in the title, change "METABOLITIES" to --METABOLITES--.

Signed and Sealed this

Fourteenth Day of September, 1993

Attest:

BRUCE LEHMAN

*Attesting Officer*     *Commissioner of Patents and Trademarks*